US 9,707,126 B2

(12) United States Patent
Friedman et al.

(10) Patent No.: US 9,707,126 B2
(45) Date of Patent: Jul. 18, 2017

(54) SYSTEMS AND METHODS FOR CORNEAL CROSS-LINKING WITH PULSED LIGHT

(71) Applicant: Avedro, Inc., Waltham, MA (US)

(72) Inventors: Marc D. Friedman, Needham, MA (US); Pavel Kamaev, Lexington, MA (US); Evan Sherr, Ashland, MA (US); William Eddington, Cambridge, MA (US); Sara Rood-Ojalvo, Boston, MA (US); David Muller, Boston, MA (US)

(73) Assignee: Avedro, Inc., Waltham, MA (US)

( * ) Notice: Subject to any disclaimer, the term of this patent is extended or adjusted under 35 U.S.C. 154(b) by 130 days.

(21) Appl. No.: 13/665,495

(22) Filed: Oct. 31, 2012

(65) Prior Publication Data

US 2013/0060187 A1  Mar. 7, 2013

Related U.S. Application Data

(63) Continuation-in-part of application No. 12/909,228, filed on Oct. 21, 2010, now Pat. No. 8,574,277.
(Continued)

(51) Int. Cl.
*A61M 37/00* (2006.01)
*A61F 9/00* (2006.01)
(Continued)

(52) U.S. Cl.
CPC .......... *A61F 9/0008* (2013.01); *A61F 9/0079* (2013.01); *A61K 31/525* (2013.01);
(Continued)

(58) Field of Classification Search
CPC .............. A61F 9/0008; A61F 9/008; A61F 2210/0085; A61F 2009/00872;
(Continued)

(56) References Cited

U.S. PATENT DOCUMENTS 4,034,750 A  7/1977  Seiderman
4,161,013 A  7/1979  Grodzinsky et al.
(Continued)

FOREIGN PATENT DOCUMENTS

DE  10 2008 046834  3/2010
EP  1 561 440 A1  8/2005
(Continued)

OTHER PUBLICATIONS

Kamaev et al. ("Photochemical Kinetics of Corneal Cross-Linking with Riboflavin", Investigative Ophthalmology & Visual Science, Apr. 2012, vol. 53, No. 4).*
(Continued)

*Primary Examiner* — Gary Jackson
*Assistant Examiner* — Scott T Luan
(74) *Attorney, Agent, or Firm* — McDonnell Boehnen Hulbert & Berghoff LLP

(57) ABSTRACT

A method for controlling activation of Riboflavin applied to an eye includes applying the Riboflavin to a selected region of a cornea of the eye and initiating cross-linking activity in the selected region by activating the Riboflavin with pulsed light illumination. The pulsed light illumination has an irradiance, dose, and an on/off duty cycle. The irradiance, the dose, and the on/off duty cycle are adjusted in response to a determination of photochemical kinetic pathways for Riboflavin cross-linking activity and to control photochemical efficiency.

21 Claims, 15 Drawing Sheets

Related U.S. Application Data

(60) Provisional application No. 61/253,736, filed on Oct. 21, 2009, provisional application No. 61/699,226, filed on Sep. 10, 2012, provisional application No. 61/671,798, filed on Jul. 16, 2012.

(51) Int. Cl.
*A61F 9/007* (2006.01)
*A61N 5/06* (2006.01)
*A61K 41/00* (2006.01)
*A61K 31/525* (2006.01)
*A61F 9/013* (2006.01)
*A61F 9/008* (2006.01)

(52) U.S. Cl.
CPC .............. *A61K 41/00* (2013.01); *A61N 5/062* (2013.01); *A61F 9/013* (2013.01); *A61F 2009/00872* (2013.01)

(58) Field of Classification Search
CPC ....... A61F 9/013; A61F 9/0079; A61N 5/062; A61K 31/525; A61K 41/00
See application file for complete search history.

(56) References Cited

U.S. PATENT DOCUMENTS

| | | |
|---|---|---|
| 4,326,529 A | 4/1982 | Doss et al. |
| 4,381,007 A | 4/1983 | Doss |
| 4,665,913 A | 5/1987 | L'Esperance, Jr. et al. |
| 4,712,543 A | 12/1987 | Baron |
| 4,764,007 A | 8/1988 | Task |
| 4,805,616 A | 2/1989 | Pao |
| 4,881,543 A | 11/1989 | Trembly et al. |
| 4,891,043 A | 1/1990 | Zeimer et al. |
| 4,969,912 A | 11/1990 | Kelman et al. |
| 4,994,058 A | 2/1991 | Raven et al. |
| 5,016,615 A | 5/1991 | Driller et al. |
| 5,019,074 A | 5/1991 | Muller |
| 5,103,005 A | 4/1992 | Gyure et al. |
| 5,171,254 A | 12/1992 | Sher |
| 5,171,318 A | 12/1992 | Gibson et al. |
| 5,281,211 A | 1/1994 | Parel et al. |
| 5,332,802 A | 7/1994 | Kelman et al. |
| 5,461,212 A | 10/1995 | Seiler et al. |
| 5,490,849 A | 2/1996 | Smith |
| 5,512,966 A | 4/1996 | Snook |
| 5,562,656 A | 10/1996 | Sumiya |
| 5,618,284 A | 4/1997 | Sand |
| 5,634,921 A | 6/1997 | Hood et al. |
| 5,766,171 A | 6/1998 | Silvestrini |
| 5,779,696 A | 7/1998 | Berry et al. |
| 5,786,893 A | 7/1998 | Fink et al. |
| 5,814,040 A | 9/1998 | Nelson et al. |
| 5,885,275 A | 3/1999 | Muller |
| 5,891,131 A | 4/1999 | Rajan et al. |
| 5,910,110 A | 6/1999 | Bastable |
| 6,033,396 A | 3/2000 | Huang et al. |
| 6,099,521 A | 8/2000 | Shadduck |
| 6,101,411 A | 8/2000 | Newsome |
| 6,104,959 A | 8/2000 | Spertell |
| 6,139,876 A | 10/2000 | Kolta |
| 6,161,544 A | 12/2000 | DeVore et al. |
| 6,162,210 A | 12/2000 | Shadduck |
| 6,188,500 B1 | 2/2001 | Rudeen et al. |
| 6,218,360 B1 | 4/2001 | Cintron et al. |
| 6,223,075 B1 | 4/2001 | Beck et al. |
| 6,270,221 B1 | 8/2001 | Liang et al. |
| 6,293,938 B1 | 9/2001 | Muller et al. |
| 6,319,273 B1 | 11/2001 | Chen et al. |
| 6,322,557 B1 | 11/2001 | Nikolaevich et al. |
| 6,325,792 B1 | 12/2001 | Swinger et al. |
| 6,334,074 B1 | 12/2001 | Spertell |
| 6,342,053 B1 | 1/2002 | Berry |
| 6,402,739 B1 | 6/2002 | Neev |
| 6,413,255 B1 | 7/2002 | Stern |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 | 3/2003 | Karageozian et al. |
| 6,571,118 B1 | 5/2003 | Utzinger et al. |
| 6,572,849 B2 | 6/2003 | Shahinian, Jr. |
| 6,617,963 B1 | 9/2003 | Watters et al. |
| 6,673,067 B1 | 1/2004 | Peyman |
| 6,918,904 B1 | 7/2005 | Peyman |
| 6,946,440 B1 | 9/2005 | DeWoolfson et al. |
| 7,001,374 B2 | 2/2006 | Peyman |
| 7,004,902 B2 | 2/2006 | Luce |
| 7,044,945 B2 | 5/2006 | Sand |
| 7,073,510 B2 | 7/2006 | Redmond et al. |
| 7,130,835 B2 | 10/2006 | Cox et al. |
| 7,141,049 B2 | 11/2006 | Stern et al. |
| 7,192,429 B2 | 3/2007 | Trembly |
| 7,270,658 B2 | 9/2007 | Woloszko et al. |
| 7,331,350 B2 | 2/2008 | Kochevar et al. |
| 7,402,562 B2 | 7/2008 | DeWoolfson et al. |
| 7,753,943 B2 | 7/2010 | Strong |
| 7,898,656 B2 | 3/2011 | Yun et al. |
| 7,935,058 B2 | 5/2011 | Dupps et al. |
| 8,111,394 B1 | 2/2012 | Borysow et al. |
| 8,115,919 B2 | 2/2012 | Yun et al. |
| 8,366,689 B2 | 2/2013 | Marshall et al. |
| 8,414,911 B2 | 4/2013 | Mattson et al. |
| 8,475,437 B2 | 7/2013 | Mrochen et al. |
| 2001/0041856 A1 | 11/2001 | McDaniel |
| 2001/0055095 A1 | 12/2001 | D'Souza et al. |
| 2002/0002369 A1 | 1/2002 | Hood |
| 2002/0013577 A1 | 1/2002 | Frey et al. |
| 2002/0049437 A1 | 4/2002 | Silvestrini |
| 2002/0099363 A1 | 7/2002 | Woodward et al. |
| 2002/0159618 A1 | 10/2002 | Freeman et al. |
| 2002/0164379 A1 | 11/2002 | Nishihara et al. |
| 2003/0018255 A1 | 1/2003 | Martin et al. |
| 2003/0175259 A1 | 9/2003 | Karageozian et al. |
| 2003/0189689 A1 | 10/2003 | Rathjen |
| 2003/0216728 A1 | 11/2003 | Stern et al. |
| 2003/0231285 A1 | 12/2003 | Ferguson |
| 2004/0001821 A1 | 1/2004 | Silver et al. |
| 2004/0002694 A1 | 1/2004 | Pawlowski et al. |
| 2004/0071778 A1 | 4/2004 | Bellmann et al. |
| 2004/0093046 A1 | 5/2004 | Sand |
| 2004/0111086 A1 | 6/2004 | Trembly et al. |
| 2004/0143250 A1 | 7/2004 | Trembly |
| 2004/0199079 A1 | 10/2004 | Chuck et al. |
| 2004/0199158 A1 | 10/2004 | Hood et al. |
| 2004/0204707 A1 | 10/2004 | Hood et al. |
| 2004/0243160 A1 | 12/2004 | Shiuey et al. |
| 2005/0038471 A1 | 2/2005 | Chan et al. |
| 2005/0096515 A1 | 5/2005 | Geng |
| 2005/0149006 A1 | 7/2005 | Peyman |
| 2005/0271590 A1 | 12/2005 | Schwartz et al. |
| 2006/0135957 A1 | 6/2006 | Panescu |
| 2006/0149343 A1 | 7/2006 | Altshuler et al. |
| 2006/0177430 A1 | 8/2006 | Bhushan et al. |
| 2006/0189964 A1 | 8/2006 | Anderson et al. |
| 2006/0195076 A1 | 8/2006 | Blumenkranz et al. |
| 2006/0276777 A1 | 12/2006 | Coroneo |
| 2006/0287662 A1 | 12/2006 | Berry et al. |
| 2007/0024860 A1 | 2/2007 | Tobiason et al. |
| 2007/0027509 A1 | 2/2007 | Eisenberg et al. |
| 2007/0048340 A1 | 3/2007 | Ferren et al. |
| 2007/0055227 A1 | 3/2007 | Khalaj et al. |
| 2007/0074722 A1 | 4/2007 | Giroux et al. |
| 2007/0099966 A1 | 5/2007 | Fabricant |
| 2007/0123845 A1 | 5/2007 | Lubatschowski |
| 2007/0135805 A1 | 6/2007 | Peyman |
| 2007/0142828 A1 | 6/2007 | Peyman |
| 2007/0161976 A1 | 7/2007 | Trembly |
| 2007/0203547 A1 | 8/2007 | Costello et al. |
| 2007/0244470 A1 | 10/2007 | Barker et al. |
| 2007/0244496 A1 | 10/2007 | Hellenkamp |
| 2007/0265603 A1 | 11/2007 | Pinelli |
| 2008/0009901 A1 | 1/2008 | Redmond et al. |
| 2008/0015660 A1* | 1/2008 | Herekar .................. 607/88 |

(56) References Cited

U.S. PATENT DOCUMENTS

| | | |
|---|---|---|
| 2008/0027328 A1 | 1/2008 | Klopotek et al. |
| 2008/0063627 A1 | 3/2008 | Stucke et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0024117 A1 | 1/2009 | Muller |
| 2009/0054879 A1 | 2/2009 | Berry |
| 2009/0069798 A1 | 3/2009 | Muller et al. |
| 2009/0116096 A1 | 5/2009 | Zalevsky et al. |
| 2009/0130176 A1 | 5/2009 | Bossy-Nobs et al. |
| 2009/0149842 A1 | 6/2009 | Muller et al. |
| 2009/0149923 A1* | 6/2009 | Herekar .......................... 607/88 |
| 2009/0171305 A1 | 7/2009 | El Hage |
| 2009/0192437 A1 | 7/2009 | Soltz et al. |
| 2009/0209954 A1 | 8/2009 | Muller et al. |
| 2009/0234335 A1 | 9/2009 | Yee |
| 2009/0271155 A1 | 10/2009 | Dupps et al. |
| 2009/0275929 A1 | 11/2009 | Zickler |
| 2009/0276042 A1 | 11/2009 | Hughes et al. |
| 2010/0028407 A1 | 2/2010 | Del Priore et al. |
| 2010/0036488 A1 | 2/2010 | De Juan, Jr. et al. |
| 2010/0057060 A1 | 3/2010 | Herekar |
| 2010/0069894 A1 | 3/2010 | Mrochen et al. |
| 2010/0082018 A1 | 4/2010 | Panthakey |
| 2010/0094197 A1 | 4/2010 | Marshall et al. |
| 2010/0114109 A1 | 5/2010 | Peyman |
| 2010/0149487 A1 | 6/2010 | Ribak |
| 2010/0149842 A1 | 6/2010 | McPhalen et al. |
| 2010/0173019 A1 | 7/2010 | Paik et al. |
| 2010/0189817 A1 | 7/2010 | Krueger et al. |
| 2010/0191228 A1 | 7/2010 | Ruiz et al. |
| 2010/0203103 A1 | 8/2010 | Dana et al. |
| 2010/0204584 A1 | 8/2010 | Ornberg et al. |
| 2010/0210996 A1 | 8/2010 | Peyman |
| 2010/0286156 A1 | 11/2010 | Pinelli |
| 2010/0318017 A1 | 12/2010 | Lewis et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0152219 A1 | 6/2011 | Stagni et al. |
| 2011/0190742 A1 | 8/2011 | Anisimov |
| 2011/0202114 A1 | 8/2011 | Kessel et al. |
| 2011/0208300 A1 | 8/2011 | de Juan, Jr. et al. |
| 2011/0237999 A1 | 9/2011 | Muller et al. |
| 2011/0264082 A1 | 10/2011 | Mrochen et al. |
| 2011/0288466 A1 | 11/2011 | Muller et al. |
| 2011/0301524 A1 | 12/2011 | Bueler et al. |
| 2012/0083772 A1 | 4/2012 | Rubinfield et al. |
| 2012/0203051 A1 | 8/2012 | Brooks et al. |
| 2012/0203161 A1 | 8/2012 | Herekar |
| 2012/0215155 A1 | 8/2012 | Muller et al. |
| 2012/0283621 A1 | 11/2012 | Muller et al. |
| 2012/0289886 A1 | 11/2012 | Muller et al. |
| 2012/0302862 A1 | 11/2012 | Yun et al. |
| 2012/0303008 A1 | 11/2012 | Muller et al. |
| 2012/0310083 A1 | 12/2012 | Friedman et al. |
| 2012/0310223 A1 | 12/2012 | Knox et al. |
| 2013/0085370 A1 | 4/2013 | Friedman et al. |
| 2013/0116571 A1 | 5/2013 | Russmann |
| 2014/0194957 A1 | 7/2014 | Rubinfeld et al. |
| 2014/0249509 A1 | 9/2014 | Rubinfeld et al. |

FOREIGN PATENT DOCUMENTS

| | | |
|---|---|---|
| EP | 1 790 383 A1 | 5/2007 |
| EP | 2 253 321 A1 | 11/2010 |
| EP | 2 490 621 | 8/2012 |
| IT | MI2010A001236 | 5/2010 |
| KG | 1376 | 8/2011 |
| RU | 2086215 | 8/1997 |
| RU | 2098057 | 12/1997 |
| RU | 2121825 | 11/1998 |
| RU | 2127099 | 3/1999 |
| RU | 2127100 | 3/1999 |
| RU | 2309713 | 11/2007 |
| RU | 2359716 | 6/2009 |
| RU | 2420330 | 6/2011 |
| RU | 2428152 | 9/2011 |
| RU | 2456971 | 7/2012 |
| WO | WO 00/74648 A2 | 12/2000 |
| WO | WO 01/58495 | 8/2001 |
| WO | WO 2004/052223 A2 | 6/2004 |
| WO | WO 2005/110397 A1 | 11/2005 |
| WO | WO 2006/012947 A2 | 2/2006 |
| WO | WO 2006/128038 A2 | 11/2006 |
| WO | WO 2007/001926 A2 | 1/2007 |
| WO | WO 2007/053826 | 5/2007 |
| WO | WO 2007/081750 | 7/2007 |
| WO | WO 2007/120457 A2 | 10/2007 |
| WO | WO 2007/139927 | 12/2007 |
| WO | WO 2007/143111 A2 | 12/2007 |
| WO | WO 2008/000478 A1 | 1/2008 |
| WO | WO 2008/052081 | 5/2008 |
| WO | WO 2008/095075 | 8/2008 |
| WO | WO 2009/073213 | 6/2009 |
| WO | WO 2009/114513 | 9/2009 |
| WO | WO 2009/146151 A2 | 12/2009 |
| WO | WO 2010/011119 A1 | 1/2010 |
| WO | WO 2010/015255 | 2/2010 |
| WO | WO 2010/023705 A1 | 3/2010 |
| WO | 2010/093908 | 8/2010 |
| WO | WO 2011/019940 | 2/2011 |
| WO | WO 2011/116306 | 9/2011 |
| WO | 2012/004726 | 1/2012 |
| WO | WO 2012/047307 | 4/2012 |
| WO | WO 2012/149570 | 11/2012 |
| WO | WO 2012/174453 | 12/2012 |
| WO | WO 2013/148713 | 10/2013 |
| WO | WO 2013/148895 | 10/2013 |
| WO | WO 2013/148896 | 10/2013 |
| WO | WO 2013/149075 | 10/2013 |
| WO | WO 2014/202736 | 12/2014 |

OTHER PUBLICATIONS

Frucht-Pery, et al. "Iontophoresis—gentamicin delivery into the rabbit cornea, using a hydrogel delivery probe," Jun. 20, 2003 (5 pages).

International Search Report and Written Opinion mailed Feb. 6, 2014 which issued in International Patent Application No. PCT/US2013/068588 (6 pages).

Koller, T. et. Al., "Complication and failure rates after corneal crosslinking," *Journal Cataract and refractive surgery*, vol. 35, No. 8, Aug. 2009, pp. 1358-1362.

Averianova, O. S., "Nastoyaschee I buduschee kross-linkage." Mir Ofalmologii, 2010, [online] [retrieved on Feb. 13, 2014] Retrieved from the internet: http://miroft.org.ua/publications/.html (3 pages).

Marzouky, et. al., Tensioactive-mediated Transepithelial Corneal Cross-linking—First Laboratory Report, European Ophthalmic Review, 2009, 3(2), pp. 67-70.

O.V. Shilenskaya et al., "Vtorichnaya katarakta posle implantatsii myagkikh IOL," [online] Aug. 21, 2008 [retrieved Mar. 4, 2013] Retrieved from the Internet: <URL:http://www.reper.ru/rus/index.php?catid=210> (4 pages).

Thorton, I. et. al., "Biomechancial Effects of Intraocular Pressure Elevation on Optic Berve/Lamina Cribrosa before and after Peripapillary Scleral Collagen Cross-Linking." Invest. Ophthalm,ol. Vis. Sci., Mar. 2009, 50(3): pp. 1227-1233.

Zhang, Y. et al., "Effect of the Synthetic NC-1059 Peptide on Diffusion of Riboflavin Across an Intact Corneal Epithelium", May 6, 2012 ARBO 2012 Annual Meeting Abstract, 140 Stroma and Keratocytes, program No. 1073, poster board number: A109 (1 page).

Kornilovsky, I. M. "Novye neinvazivnye tekhnologii lazernoy modifikatsii optiko-refraksionnykk struktur glaza. Refraktsionnaya khirurgiya I oftalmologiya." vol. 9, No. 3, 2006 (pp. 17-26).

Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].

(56) References Cited

OTHER PUBLICATIONS

International Search Report and Written Opinion mailed Jul. 18, 2013 which issued in International Patent Application No. PCT/US2013/032567 (6 pages).
Zang, Y. et al., "Effects of Ultraviolet—A and Riboflavin on the Interaction of Collagen and Proteoglycans during Corneal Cross-linking", Journal of Biological Chemistry, vol. 286, No. 15, dated Apr. 15, 2011 (pp. 13011-13022).
Search report and written opinion for Int'l Appl. No. PCT/US2012/062843, dated Apr. 11, 2013 (8 pages).
Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).
Nesterov, A. P. "Transpalpebralny Tonometr Dlya Izmereniya Vnutriglaznogo Davleniya." Feb. 2, 2006. [online] [Retrieved Dec. 17, 2012] Retrieved from the Internet: <URL: http://grpz.ru/images/publication_pdf/27.pdf>.
International Search Report and Written Opinion mailed Dec. 21, 2010 which issued in corresponding International Patent Application No. PCT/US2010/053551 (14 pages).
Li, C. et al. "Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).
Li, C. et al. "Noncontact All-Optical Measurement of Corneal Elasticity." Optics Letters. vol. 37, No. 10, May 15, 2012 (pp. 1625-1627).
Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).
Pinelli, R. "Corneal Cross-Linking with Riboflavin: Entering a New Era in Ophthalmology." Ophthalmology Times Europe. vol. 2, No. 7, Sep. 1, 2006 (3 pages).
Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).
Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164 (6 pages).
Barbarino, S. et al., "Post-LASIK ectasia: Stabilization and Effective Management with Riboflavin / ultraviolet A-induced collagen cross-linking," Association for Research in Vision and Ophthalmology, 2006 (1 page).
Burke, JM et al., Abstract for "Retinal proliferation in response to vitreous hemoglobin or iron", Investigative Ophthalmology & Visual Science, May 1981, 20(5), pp. 582-592 (1 page).
Chace, KV. et al., Abstract for "The role of nonenzymatic glycosylation, transition metals, and free radicals in the formation of collagen aggregates", Arch Biochem Biophys., Aug. 1, 1991, 288(2), pp. 473-480 (1 page).
Friedman, M. et al. "Advanced Corneal Cross-Linking System with Fluorescence Dosimetry", Journal of Ophthalmology, vol. 2012, Article ID 303459, dated May 7, 2012 (6 pages).
Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.
Kanellopoulos, A. J., "Keratoconus management: UVA-induced collagen cross-linking followed by a limited topo-guided surface excimer ablation," American Academy of Ophthalmology, 2006 (25 pages).
Kanellopoulos, A. J., "Ultraviolet a cornea collagen cross-linking, as a pre-treatment for surface excimer ablation in the management of keratoconus and post-LASIK ectasia," American Academy of Ophthalmology, 2005 (28 pages).
Meek, K.M. et al. "The Cornea and Sclera", Collagen: Structure and Mechanics, Chapter 13, pp. 359-396, 2008 (38 pages).
Pinelli, R., "Panel Discussion: Epithelium On/Off, Corneal abrasion for CCL contra", presented at the 3° International Congress of Corneal Cross Linking on Dec. 7-8, 2007 in Zurich (36 pages).
Pinelli R., "Resultados de la Sociedad de Cirugia Refractiva Italiana (SICR) utilizando el C3-R" presented at the Istitutor Laser Microchirurgia Oculare in 2007 in Italy (23 pages).
Pinelli R., "The Italian Refractive Surgery Society (SICR) results using C3-R" presented Jun. 22-23, 2007 in Italy (13 pages).
Randall, J. et al., "The Measurementand Intrepretation of Brillouin Scattering in the Lens of the Eye," The Royal Society, Abstract only, published 2013 [available online at http://rspb.royalsocietypublishing.org/content/214/1197/449.short] (1 page).
Reiss, S. et al., "Non-Invasive, ortsaufgeloeste Bestimmung von Gewebeeigenschaften derAugenlinse, Dichte undProteinkonzentration unter Anwendung der Brillouin-spektroskopie", Klin Monatsbl Augenheilkd, vol. 228, No. 12, pp. 1079-1085, Dec. 13, 2011 (7 pages).
Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).
Scarcelli, G. et al., "Brillouin Optical Microscopy for Corneal Biomechanics", Investigative Ophthalmology & Visual Science, Jan. 2012, vol. 53, No. 1, pp. 185-190 (6 pages).
Sun, G.J. et al., Abstract for "Properties of 2,3-butanedione and 1-phenyl-1,2-propanedione as new photosensitizers for visible light cured dental resin composites", Polymer 41, pp. 6205-6212, published in 2000 (1 page).
Tomlinson, A. "Tear Film Osmolarity: Determination of a Referent for Dry Eye Diagnosis", Investigative Ophthalmology & Visual Science, Oct. 2006, vol. 47, No. 10, pp. 4309-4315 (7 pages).
Turgunbaev N. A. et al. Fotomodifikatsiya sklery u bolnykh s progressiruyuschei blizorukostyu (predvaritelnoe soobschenie). 2010 [online] Retrieved from the Internet:<URL: http://www.eyepress.ru/article.aspx?7484>(2 pages).
Wong, J. et al., "Post-Lasik ectasia: PRK following previous stablization and effective management with Riboflavin / ultraviolet A-induced collagen cross-linking," Association for Research in Vision and Ophthalmology, 2006 (1 page).
Acosta A. et al., "Corneal Stroma Regeneration in Felines After Supradescemetic Keratoprothesis Implantation," *Cornea*, vol. 25, No. 7, pp. 830-838; Aug. 2006 (9 pages).
Baier J. et al., "Singlet Oxygen Generation by UVA Light Exposure of Endogenous Photosensitizers," *Biophysical Journal*, vol. 91(4), pp. 1452-1459; Aug. 15, 2006 (8 pages).
Ballou, D. et al., "Direct Demonstration of Superoxide Anion Production During The Oxidation of Reduced Flavin and of Its Catalytic Decomposition by Erythrocuprein," Biochemical and Biophysical Research Communications vol. 36, No. 6, pp. 898-904, Jul. 11, 1969 (7 pages).
Berjano E., et al., "Radio-Frequency Heating of the Cornea: Theoretical Model and in Vitro Experiments," *IEEE Transactions on Biomedical Engineering*, vol. 49, No. 3, pp. 196-205; Mar. 2002 (10 pages).
Berjano E., et al., "Ring Electrode for Radio-frequency Heating of the Cornea: Modelling and in vitro Experiments," *Medical & Biological Engineering & Computing*, vol. 41, pp. 630-639; Jun. 2003 (10 pages).
Brüel, A., "Changes in Biomechanical Properties, Composition of Collagen and Elastin, and Advanced Glycation Endproducts of The Rat Aorta in Relation to Age," Atherosclerosis 127, Mar. 14, 1996 (11 pages).
Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238 (8 pages).
Chan B.P., et al., "Effects of photochemical crosslinking on the microstructure of collagen and a feasibility study on controlled protein release;" *Acta Biomaterialia*, vol. 4, Issue 6, pp. 1627-1636; Jul. 1, 2008 (10 pages).
Chandonnet, "CO2 Laser Annular Thermokeratoplasty: A Preliminary Study," *Lasers in Surgery and Medicine*, vol. 12, pp. 264-273; 1992 (10 pages).

(56) References Cited

OTHER PUBLICATIONS

Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011 (3 pages).

Corbett M., et al., "Effect of Collagenase Inhibitors on Corneal Haze after PRK," *Exp. Eye Res.*, vol. 72, Issue 3, pp. 253-259; Jan. 2001 (7 pages).

Coskenseven E. et al., "Comparative Study of Corneal Collagen Cross-linking With Riboflaving and UVA Irradiation in Patients With Keratoconus," *Journal of Refractive Surgery*, vol. 25, issue 4, pp. 371-376; Apr. 2009 (6 pages).

"Definity (perflutren) injection, suspension [Bristol-Myers Squibb Medical Imaging]," http://dailymed.nlm.nih.gov/dailymed/drugInfo.cfm?id=8338, revised Sep. 2008, retrieved via the internet archive from http://web.archive.org/web/20100321105500/http://dailymed.nlm.nih.gov/dailymed/drugInfo.cfm?id=8338, on Dec. 14, 2011 (15 pages).

Ehlers W., et al., "Factors Affecting Therapeutic Concentration of Topical Aminocaproic Acid in Traumatic Hyphema," *Investigative Ophthalmology & Visual Science*, vol. 31, No. 11, pp. 2389-2394; Nov. 1990 (6 pages).

Erskine H., "Avedro Becomes Sponsor of US FDA Clinical Trials of Corneal Collagen Crosslinking," Press Release, Mar. 16, 2010 (1 page).

Fite et al. Noninvasive Multimodal Evaluation of Bioengineered Cartilage Constructs Combining Time-Resolved Fluorescence and Ultrasound Imaging. Tissue Eng: Part C vol. 17, No. 4, 2011 (10 pages).

Gibson, Q. et al., "The Oxidation of Reduced Flavin Mononucleotide by Molecular Oxygen," Biochem. J. (1962) 83, 368-377 (10 pages).

Glenn J.V., et al., "Advanced Glycation End Product (AGE) Accumulation on Bruch's Membrane: Links to Age-Related RPE Dysfunction;" *Investigative Ophthalmology & Visual Science*, vol. 50, No. 1, pp. 441-451; Jan. 2009 (11 pages).

Gravitz L., "Laser Show in the Surgical Suite: Lasers and a century-old dye could supplant needles and thread;" *technology review*, MIT, Mar./Apr. 2009; retrieved from http://www.technologyreview.com/biomedicine/22088/?nlid=1767, on Sep. 26, 2011 (2 pages).

Hafezi F., et al., "Collagen Crosslinking with Ultraviolet-A and Hypoosmolar Riboflavin Solution in Thin Corneas," *J. Catract Refract. Surg.*, vol. 35, No. 1, pp. 621-624; Apr. 2009 (4 pages).

Hitzenberger et al., "Birefringence Properties of the Human Cornea Measured With Polarization Sensitive Optical Coherence Tomography," Bull. Soc. Beige Ophtalmol., 302, 153-168, 2006 (16 pages).

Holmström, B. et al., "Riboflavin as an Electron Donor in Photochemical Reactions," 1867-1871, Nov. 29, 1960 (5 pages).

How to Use Definity: "Frequently Asked Questions;" retrieved from http://www.definityimaging.com/how-faq.html, on Sep. 26, 2011 (date unknown, prior to Apr. 26, 2010) (3 pages).

IMEX, "KXL System: Crosslinking Para Cirugia Corneal Bibliografia Cientifica," Product Literature, Nov. 23, 2010 (24 pages).

Kamaev et al., "Photochemical Kinetics of Corneal Cross-Linking With Riboflavin," Investigative Ophthalmology & Visual Science, Apr. 2012, vol. 53, No. 4, pp. 2360-2367 (8 pages).

Kampik D. et al., "Influence of Corneal Collagen Crosslinking With Riboflavin and Ultraviolet-A Irradiation on Excimer Laser Surgery," *Investigative Opthalmology & Visual Science*, vol. 51, No. 8, pp. 3929-3934; Aug. 2010 (6 pages).

Kissner Anja, et al., "Pharmacological Modification of the Epithelial Permeability by Benzalkonium Chloride in UVA/Riboflavin Corneal Collagen Cross-Linking," *Current Eye Research* 35(8), pp. 715-721; Mar. 2010 (7 pages).

Koller T., et al., "Therapeutische Quervernetzung der Hornhaut mittels UVA and Riboflavin: Therapeutic Cross-Linking of the Cornea Using Riboflavin/UVA," *Klinische Monatsblätter für Augenheilkunde*, vol. 224, No. 9, pp. 700-706; Sep. 2007 (7 pages).

Krueger, Ronald R., "Rapid VS Standard Collagen CXL with Equivalent Energy Dosing," presentation slides, (26 pages); available at http://www.slideshare.net/logen/krueger-herekar-rapid-cross-linking (date unknown, prior to Nov. 9, 2009).

Krueger, R. et al., "Rapid vs. Standard Collagen CXL With Equivalent Energy Dosing," posted Nov. 9, 2009 (26 pages).

Massey, V., "Activation of Molecular Oxygen by Flavins and Flavoproteins," The Journal of Biological Chemistry vol. 269, No. 36, Issue of Sep. 9, pp. 22459-22462, 1994 (4 pages).

Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).

Muller L., et al., "The Specific Architecture of the Anterior Stroma Accounts for Maintenance of Corneal Curvature," *Br. J. Opthalmol.*, vol. 85, pp. 437-443; Apr. 2001 (8 pages).

Mulroy L., et al., "Photochemical Keratodesmos for repair of Lamellar corneal Incisions;" *Investigative Ophthalmology & Visual Science*, vol. 41, No. 11, pp. 3335-3340; Oct. 2000 (6 pages).

Naoumidi T., et al., "Two-Year Follow-up of Conductive Keratoplasty for the Treatment of Hyperopic Astigmatism," *J. Cataract Refract. Surg.*, vol. 32(5), pp. 732-741; May 2006 (10 pages).

O'Neil A.C., et al., "Microvascular Anastomosis Using a Photochemical Tissue Bonding Technique;" *Lasers in Surgery and Medicine*, vol. 39, Issue 9, pp. 716-722; Oct. 2007 (7 pages).

Paddock C., Medical News Today: "Metastatic Melanoma PV-10 Trial Results Encouraging Says Drug Company;" Jun. 9, 2009; retrieved from http://www.medicalnewstoday.com/articles/153024.php, on Sep. 26, 2011 (2 pages).

Pallikaris I., et al., "Long-term Results of Conductive Keratoplasty for low to Moderate Hyperopia," *J. Cataract Refract. Surg.*, vol. 31(8), pp. 1520-1529; Aug. 2005 (10 pages).

Pinelli R., et al., "C3-Riboflaving Treatments: Where Did We Come From? Where Are We Now?" *Cataract & Refractive Surgery Today Europe*, Summer 2007, pp. 36-46; Jun. 2007 (10 pages).

Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," *J. Cataract Refract. Surgery*, vol. 35, No. 6, pp. 1055-1062; Jun. 2009 (8 pages).

Proano C.E., et al., "Photochemical Keratodesmos for Bonding Corneal Incisions;" *Investigative Ophthalmology & Visual Science*, vol. 45, No. 7, pp. 2177-2181; Jul. 2004 (5 pages).

Rocha K., et al., "Comparative Study of Riboflavin-UVA Crosslinking and "Flash-linking" Using Surface Wave Elastometry," *Journal of Refractive Surgery*, vol. 24 Issue 7, pp. S748-S751; Sep. 2008 (4 pages).

Rolandi et al. Correlation of Collagen-Linked Fluorescence and Tendon Fiber Breaking Time. Gerontology 1991;27:240-243 (4 pages).

RxList: "Definity Drug Description;" *The Internet Drug Index*, revised Jun. 16, 2008, retrieved from http://www.rxlist.com/definity-drug.htm, on Sep. 26, 2011 (4 pages).

Sheehan M., et al., "Illumination System for Corneal Collagen Crosslinking," *Optometry and Vision Science*, vol. 88, No. 4, pp. 512-524; Apr. 2011 (13 pages).

Shell, J., "Pharmacokinetics of Topically Applied Ophthalmic Drugs," *Survey of Ophthalmology*, vol. 26, No. 4, pp. 207-218; Jan.-Feb. 1982 (12 pages).

Song P., Metzler D. Photochemical Degradation of Flavins—IV. Studies of the Anaerobic Photolysis of Riboflavin. Photochemistry and Photobiology, vol. 6, pp. 691-709, 1967 (21 pages).

Sonoda S., "Gene Transfer to Corneal Epithelium and Keratocytes Mediated by Ultrasound with Microbubbles," *Investigative Ophthalmology & Visual Science*, vol. 47, No. 2, pp. 558-564; Feb. 2006 (7 pages).

Spoerl E., et al., "Artificial Stiffening of the Cornea by Induction of Intrastromal Cross-links," *Der Ophthalmologe*, vol. 94, No. 12, pp. 902-906; Dec. 1997 (5 pages).

(56) References Cited

OTHER PUBLICATIONS

Spoerl E., et al., "Induction of Cross-links in Corneal Tissue," *Experimental Eye Research*, vol. 66, Issue 1, pp. 97-103; Jan. 1998 (7 pages).

Spoerl E., et al., "Techniques for Stiffening the Cornea," *Journal of Refractive Surgery*, vol. 15, Issue 6, pp. 711-713; Nov.-Dec. 1999 (4 pages).

Spoerl E. et al., "Safety of UVA-Riboflavin Cross-Linking of the Cornea," *Cornea*, vol. 26, No. 4, pp. 385-389; May 2007 (5 pages).

Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).

Trembly et al., "Microwave Thermal Keratoplasty for Myopia: Keratoscopic Evaluation in Porcine Eyes," *Journal of Refractive Surgery*, vol. 17, No. 6, pp. 682-688; Nov./Dec. 2001 (8 pages).

"UV-X: Radiation System for Treatment of Keratokonus," *PESCHKE Meditrade GmbH*; retrieved from http://www.peschkemed.ch/ on Sep. 27, 2011 (date unknown, prior to Sep. 16, 2008) (1 page).

Vasan S., et al., "An agent cleaving glucose-derived protein crosslinks in vitro and in vivo;" *Letters to Nature*, vol. 382, pp. 275-278; Jul. 18, 1996 (4 pages).

Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).

Wollensak G., et al., "Collagen Crosslinking of Human and Porcine Sclera," *J. Cataract Refract. Surg.*, vol. 30, Issue 3, pp. 689-695; Mar. 2004 (7 pages).

Wollensak G., et al., "Riboflavin/Ultraviolet-A-induced Collagen Crosslinking for the Treatment of Keratoconus," *American Journal of Ophthalmology*, vol. 135, No. 5, pp. 620-627; May 2003 (8 pages).

Wollensak G., et al., "Cross-linking of Scleral Collagen in the Rabbit Using Riboflavin and UVA," *Acta Ophtalmologica Scandinavica*, vol. 83(4), pp. 477-482; Aug. 2005 (6 pages).

Wollensak G., "Crosslinking Treatment of Progressive Keratoconus: New Hope," *Current Opinion in Ophthalmology*, vol. 17(4), pp. 356-360; Aug. 2006 (5 pages).

Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).

Wollensak G., et al., "Biomechanical and Histological Changes After Corneal Crosslinking With and Without Epithelial Debridement," *J. Cataract Refract. Surg.*, vol. 35, Issue 3, pp. 540-546; Mar. 2009 (7 pages).

Yang H., et al., "3-D Histomorphometry of the Normal and Early Glaucomatous Monkey Optic Nerve Head: Lamina Cribrosa and Peripapillary Scleral Position and Thickness," *Investigative Ophthalmology & Visual Science*, vol. 48, No. 10, pp. 4597-4607; Oct. 2007 (11 pages).

Yang N., Oster G. Dye-sensitized photopolymerization in the presence of reversible oxygen carriers. J. Phys. Chem. 74, 856-860 (1970) (5 pages).

Zderic V., et al., "Drug Delivery Into the Eye With the Use of Ultrasound," *J. Ultrasound Med*, vol. 23(10), pp. 1349-1359; Oct. 2004 (11 pages).

Zderic V., et al., "Ultrasound-enhanced Transcorneal Drug Delivery," *Cornea* vol. 23, No. 8, pp. 804-811; Nov. 2004 (8 pages).

\* cited by examiner

SYSTEMS AND METHODS FOR CORNEAL CROSS-LINKING WITH PULSED LIGHT

CROSS REFERENCE TO RELATED APPLICATIONS

This application is a continuation-in-part of U.S. patent application Ser. No. 12/909,228, filed Oct. 21, 2010 which claims priority to U.S. Provisional Application No. 61/253,736, filed Oct. 21, 2009, the contents of these applications being incorporated entirely herein by reference. This application also claims priority to U.S. Provisional Application No. 61/699,226, filed Sep. 10, 2012 and U.S. Provisional Application No. 61/671,798, filed Jul. 16, 2012, the contents of these applications being incorporated entirely herein by reference.

BACKGROUND OF THE INVENTION

Field of the Invention

The invention pertains to systems and methods for corneal cross-linking with pulsed light, especially when a cross-linking agent is applied to stabilize desired shape changes generated in corneal tissue.

Description of Related Art

A variety of eye disorders, such as myopia, keratoconus, and hyperopia, involve abnormal shaping of the cornea. Laser-assisted in-situ keratomileusis (LASIK) is one of a number of corrective procedures that reshape the cornea so that light traveling through the cornea is properly focused onto the retina located in the back of the eye. During LASIK eye surgery, an instrument called a microkeratome is used to cut a thin flap in the cornea. The cornea is then peeled back and the underlying cornea tissue ablated to the desired shape with an excimer laser. After the desired reshaping of the cornea is achieved, the cornea flap is put back in place and the surgery is complete.

In another corrective procedure that reshapes the cornea, thermokeratoplasty provides a noninvasive procedure that applies electrical energy in the microwave or radio frequency (RF) band to the cornea. In particular, the electrical energy raises the corneal temperature until the collagen fibers in the cornea shrink at about 60° C. The onset of shrinkage is rapid, and stresses resulting from this shrinkage reshape the corneal surface. Thus, application of energy according to particular patterns, including, but not limited to, circular or annular patterns, may cause aspects of the cornea to flatten and improve vision in the eye.

The success of procedures, such as LASIK or thermokeratoplasty, in addressing eye disorders, such as myopia, keratoconus, and hyperopia, depends on determining whether the desired reshaping of the cornea has been achieved and stabilized.

BRIEF SUMMARY

One aspect of the present disclosure relates to a method for controlling activation of Riboflavin applied to an eye. The method includes applying the Riboflavin to a selected region of a cornea of the eye and initiating cross-linking activity in the selected region by activating the Riboflavin with pulsed light illumination. The pulsed light illumination has an irradiance, a dose, and an on/off duty cycle. The irradiance, the dose, and the on/off duty cycle are adjusted in response to a determination of photochemical kinetic pathways for Riboflavin cross-linking activity to control photochemical efficiency.

A further aspect of the present disclosure relates to a system for controlling cross-linking in corneal tissue. The system includes an applicator for applying a cross-linking agent to a selected region of a cornea. The system also includes a light source configured to initiate cross-linking activity in the selected region by activating the cross-linking agent. The light source is configured to deliver at least one of pulsed light illumination and continuous wave illumination. The pulsed light source has an irradiance, a dose, and an on/off duty cycle. The irradiance, the dose, and the on/off duty cycle are adjusted in response to a determination of photochemical kinetic pathways for the cross-linking activity to control photochemical efficiency and achieve a desired amount of cross-linking in the cornea. The continuous wave illumination corresponds with absorption peaks of the cross-linking agent. The system further includes a monitoring system configured to monitor the amount of cross-linking in the cornea. The irradiance, the dose and the on/off duty cycle are optionally further adjusted in response to the monitored amount of cross-linking in the cornea.

Yet another aspect of the present disclosure relates to a method of controllably applying cross-linking therapy to an eye. The method includes analyzing a cornea of the eye to determine a desired change in a biomechanical characteristic for the eye. The method further includes achieving the desired change in the biomechanical characteristic for the eye by adjusting, in response to a determination of photochemical kinetic pathways of cross-linking activity in the eye, at least one parameter selected from: an irradiance of pulsed light illumination to be applied to the cornea, a dose, a duration of an exposure cycle of the pulsed light illumination, and a duration of a dark cycle of the pulsed light illumination. The method additionally includes activating the cross-linking agent by delivering the pulsed light illumination to the cornea according to the at least one adjusted parameter.

A further aspect of the present disclosure relates to a system for dynamically controlling an amount of cross-linking in a cornea. The system includes an applicator for applying a cross-linking agent to a cornea. The system further includes a pulsed light source configured to activate the cross-linking agent. The pulsed light source has an irradiance, a dose, and an on/off duty cycle. The irradiance, the dose, and the on/off duty cycle are adjusted based on a desired amount of cross-linking in the cornea. The system additionally includes a delivery device configured to provide oxygen to a surface of the cornea.

An additional aspect of the present disclosure relates to a method for controlling cross-linking in corneal tissue. The method includes applying a cross-linking agent to a cornea and activating the cross-linking agent with pulsed light illumination. The pulsed light illumination has an irradiance, a dose, and an on/off duty cycle. The method also includes monitoring an amount of cross-linking in the cornea and adjusting the irradiance, the dose, and the on/off duty cycle in response to the monitored amount of cross-linking in the cornea. The method further includes delivering oxygen to a surface of the cornea.

These and other aspects of the present disclosure will become more apparent from the following detailed description of embodiments of the present disclosure when viewed in conjunction with the accompanying drawings.

DESCRIPTION

Figure 1:
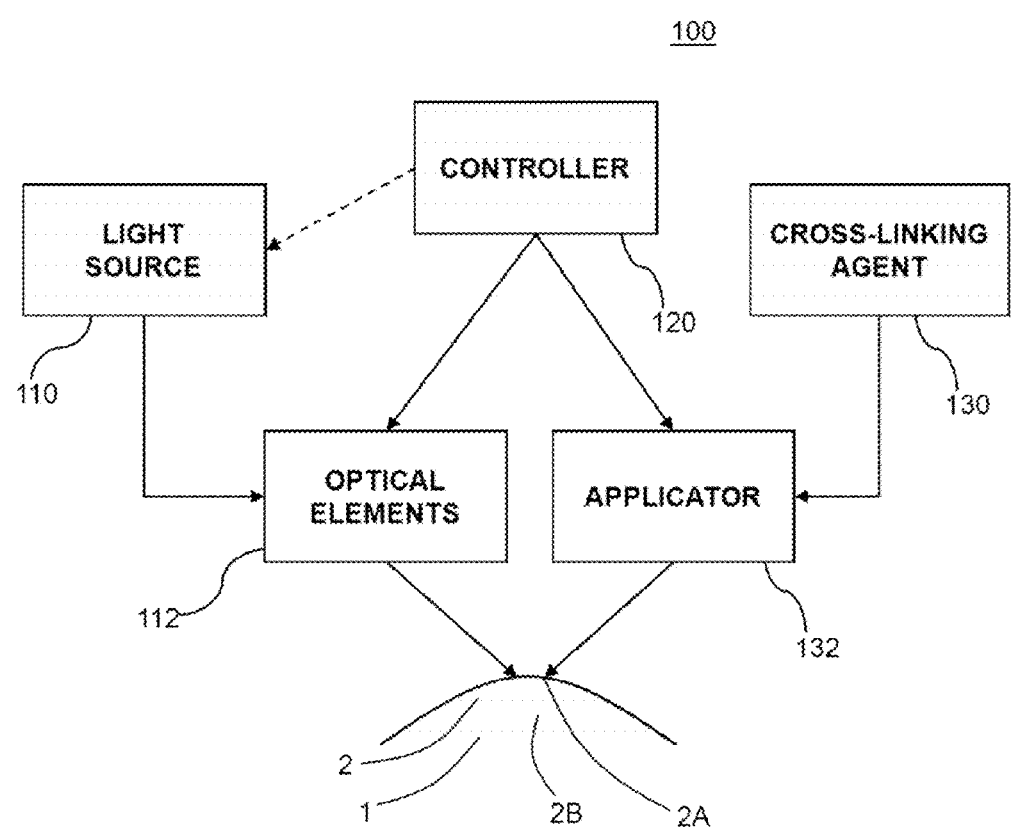
FIG. 1 provides a block diagram of an example delivery system for delivering a cross-linking agent and an activator to a cornea of an eye in order to initiate molecular cross-linking of corneal collagen within the cornea.

Aspects of the present disclosure relate to using an example delivery system 100 for delivering a cross-linking agent 130 to a cornea 2 of an eye 1 in order to initiate molecular cross-linking of corneal collagen within the cornea 2 as shown in FIG. 1. The delivery system 100 includes an applicator 132 for applying the cross-linking agent 130 to the cornea 2. The delivery system 100 includes a light source 110 and optical elements 112 for directing light to the cornea 2. The delivery system 100 also includes a controller 120 that is coupled to the applicator 132 and the optical elements 112. The applicator 132 may be an apparatus adapted to apply the cross-linking agent 130 according to particular patterns on the cornea 2. The applicator 132 may apply the cross-linking agent 130 to a corneal surface 2A (e.g., an epithelium), or to other locations on the eye 1. Particularly, the applicator 132 may apply the cross-linking agent 130 to an abrasion or cut of the corneal surface 2A to facilitate the transport or penetration of the cross-linking agent through the cornea 2 to a mid-depth region 2B.

A large number of conditions and parameters affect the cross-linking of corneal collagen with the cross-linking agent. When the initiating element is ultraviolet-A ("UVA") light, the irradiance and the dose both affect the amount and the rate of cross-linking. The UVA light may be applied continuously (continuous wave or CW) or as pulsed light, and this selection has an effect on the amount, the rate, and the extent of cross-linking. If the UVA light is applied as pulsed light, the duration of the exposure cycle, the dark cycle, and the ratio of the exposure cycle to the dark cycle duration all have an effect on both the rate of cross-linking and the amount of resulting corneal stiffening. Other factors that play a significant role in cross-linking include cross-linking agent concentration, temperature, specific conditions of the cornea (e.g., if any previous treatments have taken place), as well as other factors and parameters.

Aspects of the present disclosure relate to determining the effect of each of these parameters on the rate and the amount of cross-linking, as well as the interrelations of these parameters among each other to optimize the conditions to achieve the desired amount, rate, and location (on the cornea 2) of corneal stiffening. Aspects of the present disclosure relate to monitoring the corneal response to a change in one or a plurality of parameters and adjusting the one or the plurality of parameters based on the received feedback.

As described herein, the devices and approaches disclosed herein may be used to preserve desired shape or structural changes following an eye therapy treatment by stabilizing the corneal tissue of the cornea 2. The devices and approaches disclosed herein may also be used to enhance the strength or biomechanical structural integrity of the corneal tissue apart from any eye therapy treatment.

With reference to FIG. 1, the optical elements 112 may include one or more mirrors or lenses for directing and focusing the light emitted by the light source 110 to a particular pattern on the cornea 2 suitable for activating the cross-linking agent 130. The light source 110 may be a UVA light source that may also alternatively or additionally emit photons with greater or lesser energy levels than ultraviolet light photons. The delivery system 100 also includes a controller 120 for controlling the operation of the optical elements 112 or the applicator 132, or both. By controlling aspects of the operation of the optical elements 112 and the applicator 132, the controller 120 can control the regions of the cornea 2 that receive the cross-linking agent 130 and that are exposed to the light source 110. By controlling the regions of the cornea 2 that receive the cross-linking agent 130 and the light source 110, the controller 120 can control the particular regions of the cornea 2 that are strengthened and stabilized through cross-linking of the corneal collagen fibrils. In an implementation, the cross-linking agent 130 can be applied generally to the eye 1, without regard to a particular region of the cornea 2 requiring strengthening, but the light source 110 can be directed to a particular region of the cornea 2 requiring strengthening, to thereby control the region of the cornea 2 wherein cross-linking is initiated by controlling the regions of the cornea 2 that are exposed to the light source 110. Moreover, aspects of the present invention relate to modulating the specific regimes of the applied light to achieve a desired degree of corneal stiffening in selected regions of the cornea 2.

Another controller may be used to control the operation of the optical elements 112, and thereby control with precision the delivery of the light source 110 (i.e., the initiating element) to the cornea 2 by controlling any combination of: wavelength, bandwidth, intensity, power, location, depth of penetration, and duration (the duration of the exposure cycle, the dark cycle, and the ratio of the exposure cycle to the dark cycle duration) of treatment. In addition, the function of the controller 120 can be partially or wholly replaced by a manual operation.

Although the embodiments described herein may initiate cross-linking in the cornea according to an annular pattern defined, for example, by a thermokeratoplasty applicator, the initiation pattern in other embodiments is not limited to a particular shape. Indeed, energy may be applied to the cornea in non-annular patterns, so cross-linking may be initiated in areas of the cornea that correspond to the resulting non-annular changes in corneal structure. Examples of the non-annular shapes by which energy may be applied to the cornea are described in U.S. application Ser. No. 12/113,672, filed on May 1, 2008, the contents of which are entirely incorporated herein by reference.

Embodiments may also employ aspects of multiphoton excitation microscopy. In particular, rather than delivering a single photon of a particular wavelength to the cornea 2, the delivery system (e.g., 100 in FIG. 1) delivers multiple photons of longer wavelengths, i.e., lower energy, that combine to initiate the cross-linking Advantageously, longer wavelengths are scattered within the cornea 2 to a lesser degree than shorter wavelengths, which allows longer wavelengths of light to penetrate the cornea 2 more efficiently than shorter wavelength light. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 that release radicals (Riboflavin or photosensitizer and oxygen). When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

Aspects of the present disclosure, e.g., adjusting the parameters for delivery and activation of the cross-linking agent, can be employed to reduce the amount of time required to achieve the desired cross-linking. In an example implementation, the time can be reduced from minutes to seconds. While some configurations may apply the initiating element (i.e., the light source 110) at an irradiance of 5 mW/cm², aspects of the present disclosure allow larger irradiance of the initiating element, e.g., multiples of 5 mW/cm², to be applied to reduce the time required to achieve the desired cross-linking Highly accelerated cross-linking is particularly possible when using laser scanning technologies in combination with a feedback system. The total dose of energy absorbed in the cornea 2 can be described as an effective dose, which is an amount of energy absorbed through an area of the corneal surface 2A. For example the effective dose for a region of the corneal surface 2A can be, for example, 5 J/cm², or as high as 20 J/cm² or 30 J/cm². The effective dose described can be delivered from a single application of energy, or from repeated applications of energy.

Aspects of the present disclosure provide systems and methods for delivering pulsed light of specific duty cycle and frequency, especially when a cross-linking agent is applied to stabilize desired shape changes generated in corneal tissue. Corneal cross-linking with Riboflavin is a technique that uses UVA light to photoactivate Riboflavin to stabilize and/or reduce corneal ectasia, in diseases such as keratoconus and post-LASIK ectasia. Corneal cross-linking improves corneal strength by creating additional chemical bonds within the corneal tissue.

According to aspects of the present disclosure, systems and methods generate pulsed light by employing a digital micro-mirror device (DMD), electronically turning a light source on and off, and/or using a mechanical or opto-electronic (e.g., Pockels cells) shutter or mechanical chopper or rotating aperture. DMD technology may be used to modulate the application of initiating light spatially as well as a temporally. Using DMD technology, a controlled light source projects the initiating light in a precise spatial pattern that is created by microscopically small mirrors laid out in a matrix on a semiconductor chip, known as a DMD. Each mirror represents one or more pixels in the pattern of projected light. The power and duration at which the light is projected is determined as described elsewhere. According to other aspects of the present disclosure, pulsed light may be generated in any suitable manner.

Riboflavin is deactivated (reversibly or irreversibly) and/or photo-degraded to a greater extent as irradiance increases. When Riboflavin absorbs radiant energy, especially light, it undergoes photosensitization. There are two major photochemical kinetic pathways for Riboflavin photosensitization, Type I and Type II. Some of the major reactions involved in both the Type I and Type II mechanisms are as follows:

Common Reactions for Type I and Type II Mechanisms $$Rf \rightarrow Rf^*_1, I_{abs} \quad (1)$$

$$Rf^*_1 \rightarrow Rf, k1 \quad (2)$$

$$Rf^*_1 \rightarrow Rf^*_3, k2 \quad (3)$$

Type I Mechanism $$Rf_3^* + SH \rightarrow (RF.^- + SH.^+) \rightarrow RfH. + S., k3 \quad (4)$$

$$2RfH\cdot \rightarrow Rf+RfH_2, k4 \tag{5}$$

$$RfH_2+O_2\rightarrow Rf_{ox}+H_2O_2, k5 \tag{6}$$

Type II Mechanism $$Rf_3^*+O_2\rightarrow Rf+{}^1O_2, k6 \tag{7}$$

$$SH+{}^1O_2\rightarrow S_{ox}, k6 \tag{8}$$

Rf represents Riboflavin in the ground state. $Rf^*_1$ represents Riboflavin in the excited singlet state. $Rf^*_3$ represents Riboflavin in a triplet excited state. $Rf.^-$ is the reduced radical anion form of Riboflavin. RfH. is the radical form of Riboflavin. $RfH_2$ is the reduced form of Riboflavin. SH is the substrate. $SH.^+$ is the intermediate radical cation. S. is the radical. $S_{ox}$ is the oxidized form of the substrate. $Rf_{ox}$ is deuteroflavin (7,8-dimethyl-10-(formylmethyl)isoalloxazine) having UVA absorption and sensitizer properties similar to those of Riboflavin (and unlike those of $RfH_2$).

Riboflavin is excited into its triplet excited state $Rf^*_3$ as shown in reactions (1) to (3). From the triplet excited state $Rf^*_3$, the Riboflavin reacts further, generally according to Type I or Type II photomechanical mechanisms.

Type I mechanism above is favored at low oxygen concentrations, and Type II mechanism is favored at high oxygen concentrations. In Type I mechanism, the substrate reacts with the sensitizer excited state to generate radicals or radical ions, respectively, by hydrogen atoms or electron transfer. In Type II mechanism, the excited sensitizer reacts with oxygen to form singlet molecular oxygen. The singlet molecular oxygen then acts on tissue to produce additional cross-linked bonds.

Oxygen concentration in the cornea is modulated by UVA irradiance and temperature and quickly decreases at the beginning of UVA exposure. The oxygen concentration tends to deplete within about 10-15 seconds for irradiance of 3 $mW/cm^2$ (as shown, for example, in FIG. 2A) and within about 3-5 seconds for irradiance of 30 $mW/cm^2$. Utilizing pulsed light of a specific duty cycle, frequency, and irradiance, input from both Type I and Type II photochemical kinetic mechanisms may be optimized to achieve the greatest amount of photochemical efficiency. Moreover, utilizing pulsed light allows regulating the rate of reactions involving Riboflavin. The rate of reactions may either be increased or decreased, as needed, by regulating, one of the parameters such as the irradiance, the dose, the on/off duty cycle, Riboflavin concentration, soak time, and others. Moreover, additional ingredients that affect the reaction and cross-linking rates may be added to the cornea.

One aspect of the present disclosure relates to achieving photon optimization by allowing deactivated (reduced) Riboflavin to return to ground state Riboflavin in Type I reactions and allowing for reduced rate of oxygen uptake in Type II reactions where better photon conversion efficiency occurs.

The rate of return of deactivated (reduced) Riboflavin to ground state in Type I reactions and the rate of oxygen uptake in Type II reactions is determined by a number of factors. These factors include, but are not limited to, on/off duty cycle of pulsed light treatment, pulse rate frequency, irradiance, and dose. Moreover, the Riboflavin concentration, soak time, and addition of other agents, including oxidizers, affect the rate of oxygen uptake. These and other parameters, including duty cycle, pulse rate frequency, irradiance, and dose are optimized to achieve optimal photon efficiency and make efficient use of both Type I and Type II photochemical kinetic mechanisms for Riboflavin photosensitization. Moreover, these parameters are optimized in such a way as to achieve an optimum chemical amplification effect.

According to aspects of the present disclosure, for pulsed light treatment, the on/off duty cycle is between approximately 100/1 to approximately 1/100; the irradiance is between approximately 1 $mW/cm^2$ to approximately 500 $mW/cm^2$ average irradiance, and the pulse rate is between approximately 0.1 Hz to approximately 1000 Hz.

According to aspects of the present disclosure, for pulsed light treatment, the on/off duty cycle is between approximately 1000/1 to approximately 1/1000; the irradiance is between approximately 1 $mW/cm^2$ to approximately 1000 $mW/cm^2$ average irradiance, and the pulse rate is between approximately 1000 Hz to approximately 100,000 Hz. These averages are based on using a q-switched laser source instead of an LED system where higher repetition rates are possible. According to further aspects of the present disclosure, the laser source may be an adjustable pulsed source, an LED system, arc sources or incandescents at very long on-time duty cycles, or any other suitable sources.

Pulse rates of 0.1 Hz to approximately 1000 Hz or 1000 Hz to approximately 100,000 Hz may be chosen based on the photochemical kinetics as detailed by Kamaev et al., Investigative Ophthalmology & Visual Science, April 2012, Vol. 53, No. 4, pp. 2360-2367 (April 2012), which is incorporated herein by reference in its entirety. According to aspects of the present disclosure, the pulse length may be long—on the order of one or several seconds—or short—on the order of fractions of a second.

According to aspects of the photochemical kinetics of corneal cross-linking with Riboflavin, pulsed light illumination can be used to create greater or lesser stiffening of corneal tissue than may be achieved with continuous wave illumination for the same amount or dose of energy delivered. Light pulses of suitable length and frequency may be used to achieve optimum chemical amplification.

Figure 2A:
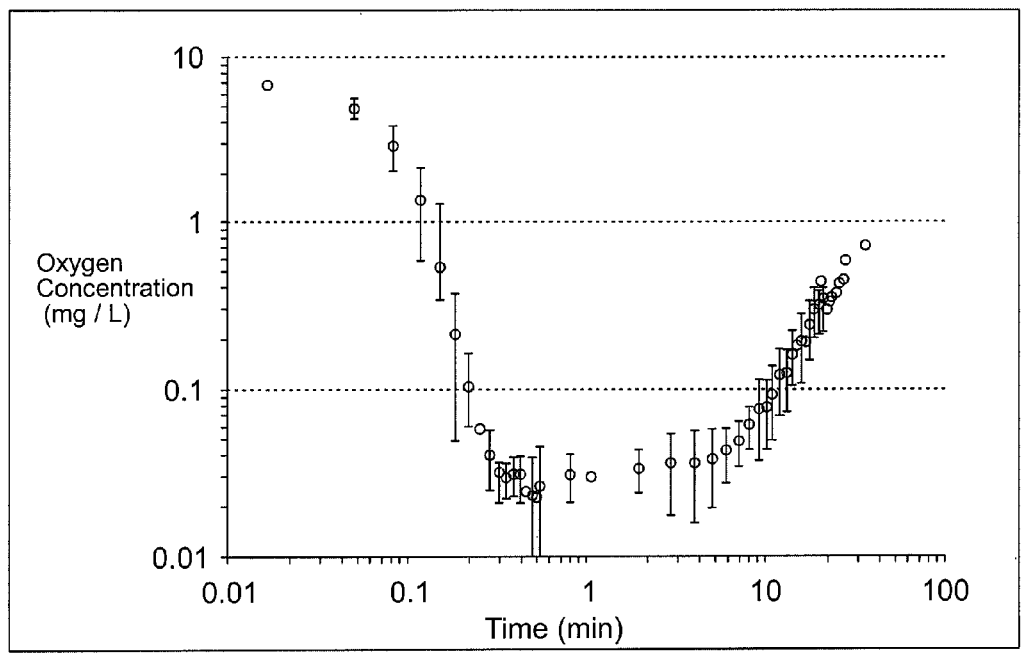
FIG. 2A illustrates a graph of depletion and gradual replenishment of oxygen below a 100 μm corneal flap saturated with 0.1% Riboflavin during 3 mW/cm² continuous wave (CW) irradiation.

FIG. 2A illustrates a graph of depletion and gradual replenishment curve of dissolved oxygen below a 100 μm thick porcine corneal flap, saturated with 0.1% Riboflavin during 3 $mW/cm^2$ UVA irradiation at 25° C. The oxygen concentration (mg/L) fell to zero at about 15 seconds and gradually started to increase after approximately 10 minutes, getting back to approximately one-tenth its starting value after 30 minutes.

Figure 2B:
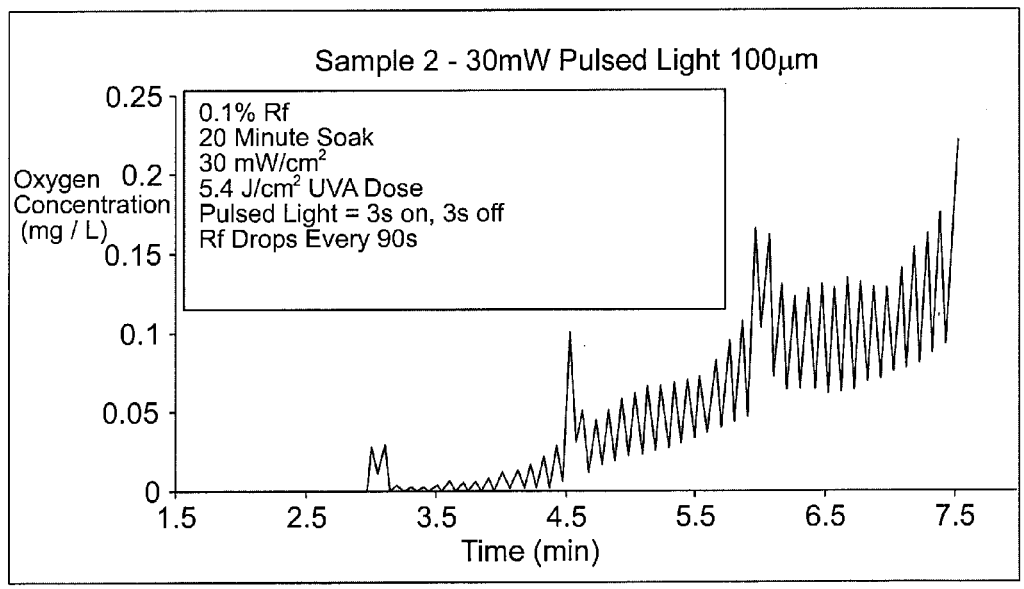
FIG. 2B illustrates a graph of oxygen recovery under a 100 μm corneal flap saturated with 0.1% Riboflavin during 30 mW/cm² pulsed irradiation.

FIG. 2B illustrates a graph of oxygen recovery under a 100 μm thick corneal flap. The corneal flap was saturated with 0.1% Riboflavin during 30 $mW/cm^2$ UVA irradiation. The irradiation was pulsed at a 3 second on/3 seconds off cycle. Riboflavin drops were added to the cornea every 90 seconds. In this example, it took about 3 minutes for the oxygen concentration to gradually start increasing and about 6 minutes for the oxygen concentration to increase to 0.1 mg/L.

Under aerobic conditions, which are present during the first 10 to 15 seconds of UVA exposure, sensitized photooxidation of the substrate (proteoglycan core proteins and collagen in the corneal matrix) occurs mainly by its reaction with photochemically generated reactive oxygen species, such as singlet molecular oxygen. This is consistent with a Type II photochemical mechanism. After the first 10 to 15 seconds, oxygen becomes totally depleted and the reaction between the substrate and Riboflavin becomes consistent with a predominantly Type I photochemical mechanism. More than halfway through the period of illumination, the oxygen concentration in the cornea slowly increases to a concentration at which a Type II mechanism may begin to play an additional role. During this phase, a growing contribution would be expected from the singlet oxygen-mediated cross-linking, together with the enhancement of secondary radical reactions that are modulated by oxygen.

Studies of corneal flaps taken at various depths after cross-linking, and tested by stress-strain behavior or collagen fluorescence analysis, suggest that corneal stiffening is primarily in the anterior 200 µm of the corneal stroma. Increase of collagen fluorescence in UVA-exposed corneas, which is related to their mechanical stiffening, can be detected at a depth 200 to 300 µm from the corneal surface as will be described further below.

If UVA radiation is stopped shortly after oxygen depletion, oxygen concentrations start to increase (replenish) as shown in FIGS. 2A and 2B. Excess oxygen may be detrimental in corneal cross-linking process because oxygen is able to inhibit free radical photopolymerization reactions by interacting with radical species to form chain-terminating peroxide molecules. The pulse rate, irradiance, dose, and other parameters may be adjusted to achieve an optimized oxygen regeneration rate. Calculating and adjusting the oxygen regeneration rate is another example of adjusting the reaction parameters to achieve a desired amount of corneal stiffening.

Dissolved free oxygen is significantly depleted not only at the position of the oxygen sensor and below, but also throughout the corneal flap above. Oxygen content may be depleted throughout the cornea, by various chemical reactions, except for the very thin corneal layer where oxygen diffusion is able to keep up with the kinetics of the reactions. This diffusion-controlled zone will gradually move deeper into the cornea as the reaction ability of the substrate to uptake oxygen decreases.

Oxygen measurements in the cornea suggest that the predominant photosensitizing mechanism for cross-linking with Riboflavin is the Type I pathway after a very short initial Type II photochemical mechanism at the start of the illumination with UVA light. More than halfway through the period of illumination, the oxygen concentration in the cornea slowly increases, as shown in FIGS. 2A and 2B above, to a concentration at which a Type II mechanism may begin to play an additional role.

The mechanism for corneal cross-linking begins with the additional pathway kinetics expressed in equation (6) above. After a short period of time (a few seconds), oxygen becomes depleted, and there is little oxygen available as shown in FIG. 2A. Under these anaerobic conditions, Leuco-Deuteroflavin+$H_2O_2$ are formed as described in Heldman et al., Handbook of Food Engineering ($2^{nd}$ Edition), CRC Press (2006). Leuco-Deuteroflavin has low absorption at 360 nm and lacks the photosensitizing ability and therefore cannot create radicals. Leuco-Deuteroflavin is referred to herein as reduced flavin, reduced Riboflavin, $RfH_2$, and $Fl_{red}H_2$.

Reduced Riboflavin undergoes an oxidation reaction as shown in equation (6) above. The oxidation of reduced Riboflavin by molecular oxygen is irreversible, autocatalytic, and involves generation of free radicals that can initiate radical polymerization (as in case of vinyl monomers, acrylamide with bis(acrylamide), etc.). The autocatalytic oxidation of reduced Riboflavins by oxygen is accounted for by the reactions described in Massey, V., Activation of molecular oxygen by flavins and flavoproteins, J. Biol. Chem. (1994), 269, 22459-22462.

Depending on the particular circumstances, there may be a need to either speed up or slow down the oxidation rate of the reduced Riboflavin. A number of parameters affect the reaction rate and cross-linking rate of the reduced Riboflavin.

During pulsed light irradiation, when the UVA light is turned off (or turned down to a lower value), following the many pathways described by Massey, oxygen is regenerated locally near the Leuco-Deuteroflavin converting it into Deuteroflavin which is able to absorb light again and thereby create radicals for cross-linking Therefore, improved photon efficiency is achieved through the proper timing of on/off cycles through the regeneration of Deuteroflavin. Regeneration of Deuteroflavin allows for larger overall concentration of radical generation for a given light energy dose than under continuous wave illumination and continuous anaerobic conditions.

Oxygen is the naturally occurring oxidizer and is used as the oxidizer according to aspects of the present disclosure. According to further aspects of the present disclosure, oxygen and/or other oxidizers are utilized; such oxidizers may be added to the formulation or administered to the cornea in a suitable way.

According to other embodiments of the present disclosure, reduced Riboflavin may be soaked in a suitable agent that contains oxygen and is able to oxidize the reduced Riboflavin. According to one embodiment, Vitamin B12 may be added in any suitable manner to the reduced Riboflavin and/or to the cornea. Vitamin B12 contains a Cobalt molecule that is capable of holding oxygen, thereby creating an oxygen storage reservoir. The reduced Riboflavin may be super-saturated with Vitamin B12 or another suitable oxygen carrying agent. The suitable agent, such as Vitamin B12, may be provided in conjunction with application of pulsed light. The proper level of oxygen can be maintained with various reversible oxygen carriers. See Yang N., Oster G. Dye-sensitized photopolymerization in the presence of reversible oxygen carriers. J. Phys. Chem. 74, 856-860 (1970), the contents of which are incorporated entirely herein by reference.

Corneal stiffening may be applied to the cornea according to particular patterns, including, but not limited to, circular or annular patterns, which may cause aspects of the cornea to flatten and improve vision in the eye. For example, more or less corneal stiffening may be desired on the outer edges of the cornea as opposed to the center of the cornea. Aspects of the present disclosure relate to achieving more corneal stiffening on the outer diameter of the cornea and gradually decreasing the amount of corneal stiffening from the outer diameter toward the center of the cornea. Other aspects of the present disclosure relate to selecting regions of the cornea that require more corneal stiffening based on a predetermined set of characteristics and applying more corneal stiffening to those selected regions by varying the regime of the pulsed light. According to certain aspect of the present disclosure, pulsed light may be applied with different irradiance, dose and/or different duty cycle to different areas of the cornea, leading to areas of differing levels of corneal stiffening or corneal stiffening gradients. Varying the regime of the pulsed light to achieve a desired level of corneal stiffening is another example of adjusting the parameters of the cross-linking reaction to achieve specific, targeted results. Moreover, varying the regime of the pulsed light to achieve a desired level of corneal stiffening at selected regions of the cornea allows for more precise and accurate control of the shape changes in the eye.

Algorithms for applying the initiating element such as UV light according to a selected pattern are described, for example, in U.S. patent application Ser. No. 13/051,699, filed Mar. 18, 2011, the contents of which are incorporated entirely herein by reference.

Currently, at least three different paths leading to cross-links may be utilized: a path through the direct attack of the excited Riboflavin's triplets (Type I mechanism), through singlet oxygen (Type II), and through the generation of free radicals when the reduced Riboflavin ($RFH_2$) interacts with oxygen (as seen in the scheme below).

The reduced form of Riboflavin $RFH_2$ (with two hydrogen atoms supplied to the aromatic nucleus by the side chain) can be produced by anaerobic photolysis of Riboflavin (Holmstrom 1961) and observed by the reduction in absorption at 445 nm.

Figure 3:
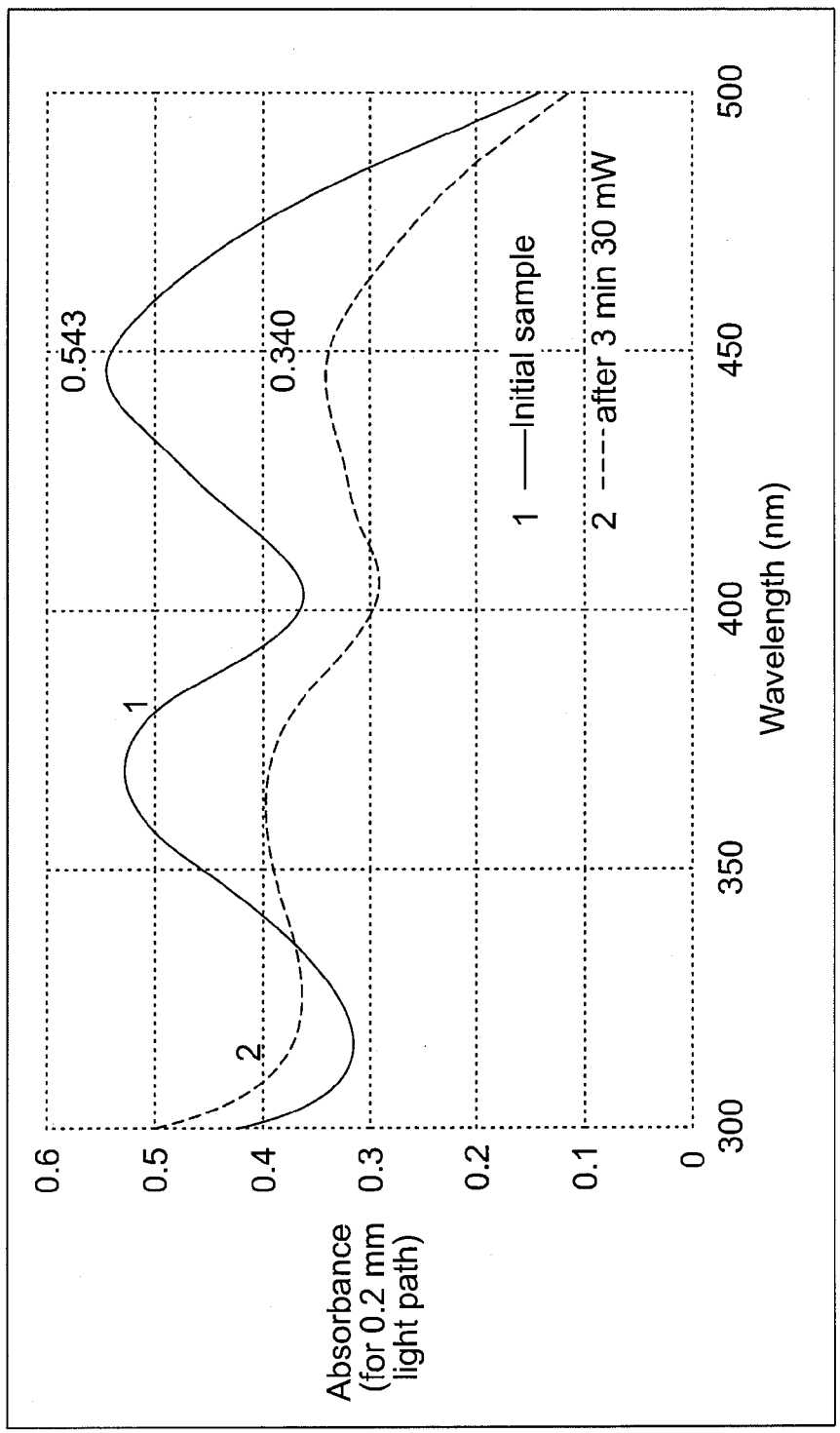
FIG. 3 illustrates a graph of absorbance of reduced Riboflavin before and after 30 mW/cm² CW irradiation for 3 minutes.

Referring now to FIG. 3, a graph illustrating absorbance for 0.2 mm light path of an initial sample of Riboflavin versus absorbance for 0.2 mm light path of reduced Riboflavin $RfH_2$ after being irradiated for 3 minutes at an irradiance of 30 mW/cm$^2$. At a wavelength of 445 nm, the absorbance of the initial sample is about 0.543, while the absorbance of the irradiated sample is about 0.340.

$RFH_2$ is autoxidizable and in the presence of oxygen yields the highly light-sensitive fluorescent and absorbing (445 nm) Deuteroflavin (7,8-dimethyl-10-(formylmethyl) isoalloxazine). Reduced Riboflavin solutions can be prepared under nitrogen by irradiation of Riboflavin with visible light in the presence of EDTA and stored in absence of oxygen. Reaction with oxygen completes during hundreds of msec (depending on the initial conditions), proceeds via free radicals (as described in Massey), and is able to initiate polymerization of vinyl monomers. The rate of the reaction with oxygen may be increased by dissolving oxygen in a flavin solution instead of in water.

Example 1—Fluorescence of Corneal Samples $RFH_2$ was prepared by irradiation of Riboflavin solutions (with and without EDTA, 1% EDTA, 0.1% Riboflavin) and saturated with argon (to displace oxygen) in a shallow sealed quartz cuvette. Then, in the absence of additional UV light, porcine corneal flaps were immediately placed in those solutions. After 1-2 min this procedure was repeated with a fresh solution containing $RFH_2$ several times. Corneal flaps then were washed with distilled water, digested with papain buffer, and their fluorescence was measured.

Figure 4A:
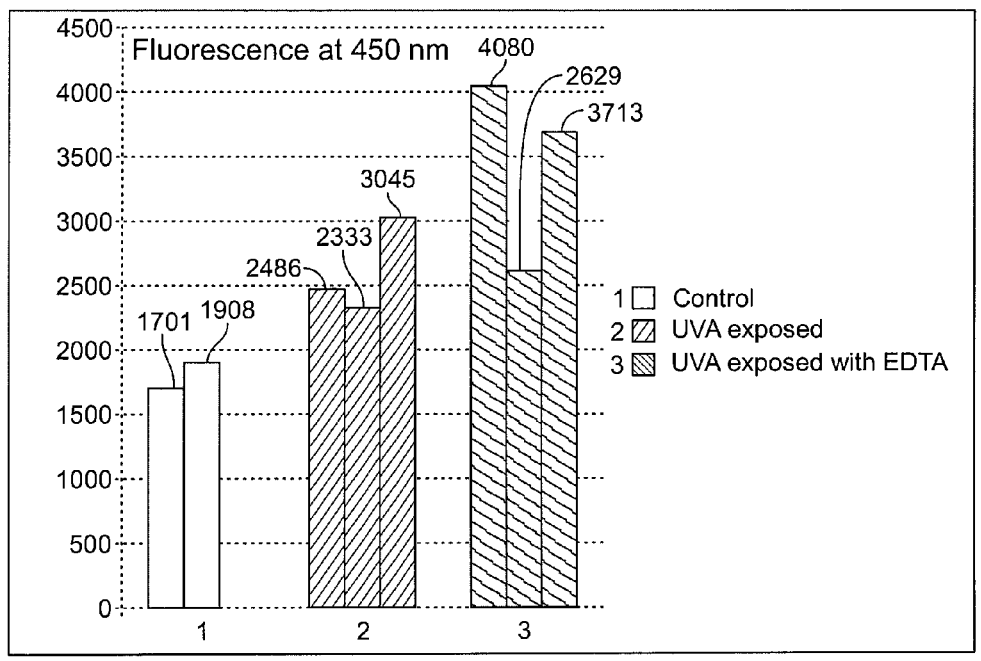
FIG. 4A illustrates a graph of fluorescence or Riboflavin samples at 450 nm.

As seen in FIG. 4A, fluorescence of the corneal samples treated with preliminary UVA-exposed Riboflavin solutions, was higher than fluorescence of the corneal samples washed with pure, unexposed Riboflavin. This can indicate that oxidation of $RFH_2$ is able to generate some cross-linking in the cornea, but observed fluorescence was significantly lower than generally observed in corneal flaps directly exposed to the UVA. The fluorescence was the highest for the sample prepared by irradiation of Riboflavin solutions with a reducing agent such as EDTA. Accordingly, one way of increasing the cross-linking efficiency of $RfH_2$ is to use Riboflavin in a solution with a reducing agent for Riboflavin. The reducing agents may include, but are not limited to, EDTA, ascorbic acid, sugars, amines, amino acids, and any combination thereof. This is another example of modifying the parameters of the cross-linking reaction to achieve a desired level of cross-linking with the corneal fibrils. According to one aspect of the present invention, Riboflavin concentrations between about 0.001% Riboflavin to about 1.0% Riboflavin may be utilized.

It was found that fluorescence intensity of collagen (as in the original material or in the material digested by enzymes like papain solution) linearly correlates with its stiffness. For example, this correlation was reported for corneal collagen in Chai et al. Quantitative Assessment of UVA-Riboflavin Corneal Cross-Linking Using Nonlinear Optical Microscopy. Investigative Opthalmology & Visual Science, June 2011, Vol. 52, No. 7 (2011), the contents of which are incorporated entirely herein by reference. This correlation was reported for collagen fibers from Wistar rats in Rolandi et al. Correlation of Collagen-Linked Fluorescence and Tendon Fiber Breaking Time. Gerontology 1991; 27:240-243, the contents of which are incorporated entirely herein by reference. This correlation was reported for collagen in chondrogetic samples in Fite et al. Noninvasive Multimodal Evaluation of Bioengineered Cartilage Constructs Combining Time-Resolved Fluorescence and Ultrasound Imaging. Tissue Eng: Part C Vol. 17, Number 4, 2011, the contents of which are incorporated entirely herein by reference. This correlation was reported for collagen network in human articular cartilage in Verzijl et al. Crosslinking by Advanced Glycation End Products Increases the Stiffness of the Collagen Network in Human Articular Cartilage. Arthritis & Rheumatism Vol. 46, No. 1, January 2002, pp. 114-123, the contents of which are incorporated entirely herein by reference.

Cross-linking efficacy tends to decrease at higher Riboflavin concentrations. See Song P., Metzler D. Photochemical Degradation of Flavins—IV. Studies of the Anaerobic Photolysis of Riboflavin. Photochemistry and Photobiology, Vol. 6, pp. 691-709, 1967, the contents of which are incorporated entirely herein by reference (explaining the shielding effect of Riboflavin and that quenching of the triplet state by Riboflavin itself (concentration quenching) must be considered, and that the products of photochemical cleavage decrease the quantum yield rapidly as they accumulate.)

Example 2—Measurement of the Collagen Linked Fluorescence in Cross-Linked Corneal Flaps at Depths of 100 μm and 200 μm Materials and Methods Porcine whole globes (SiouxPreme Packing Co., Sioux City, Iowa; shipped in saline solution packed in ice) were warmed to room temperature (25° C.). The corneas were then de-epithelialized with a dulled scalpel blade and 0.1, 0.25, or 0.5% riboflavin solution in 0.9% saline was applied to the top of each cornea during 20 minutes before cross-linking Corneas were pan-corneally irradiated with a top hat beam (3% root mean square) for a determined amount of time with 365-nm light source (UV LED NCSU033B[T]; Nichia Co., Tokushima, Japan) at the chosen irradiance (3 or 30 mW/cm$^2$) which was measured with a power sensor (model PD-300-UV; Ophir, Inc., Jerusalem, Israel) at the corneal surface.

Corneal flaps (each 100 μm thick, one after another) were excised from the eyes with aid of Intralase femtosecond laser (Abbott Medical Optics, Santa Ana, Calif.). The average thickness of the corneal flaps was calculated as a difference between the measurements before and after the excision from the eyes with an ultrasonic Pachymeter (DGH Technology, Exton, Pa.). The flaps were washed with distilled water until Riboflavin in the washing waters was not detectable by absorbance measurement at 455 nm (Thermo Scientific Evolution 300/600 UV-Vis Spectrophotometer, Thermo Fisher Scientific, Waltham, Mass.). The flaps then were dried in vacuum until the weight change became less than 10% (Rotary vane vacuum pump RV3 A652-01-903, BOC Edwards, West Sussex, UK).

Each flap (1 mg) was digested for 2 h at 65° C. with 2.5 units/ml of papain (from Papaya latex, Sigma) in 0.5 ml of papain buffer [1×PBS (pH 7.4), 2 mM L-cysteine and 2 mM EDTA]. Papain digests were centrifuged for 30 seconds at 2200×G (Mini centrifuge 05-090-100, Fisher Scientific), diluted 3 times with 1×PBS solution and fluorescence of the solutions was measured with excitation of $\lambda ex=360$ nm in a QM-40 Spectrofluorometer (Photon Technology Int., London, Ontario, Canada). The fluorescence of the papain buffer was taken into account by measuring fluorescence in the absence of tissue and subtracting this value from the fluorescence of the samples.

Results

Figure 4B:
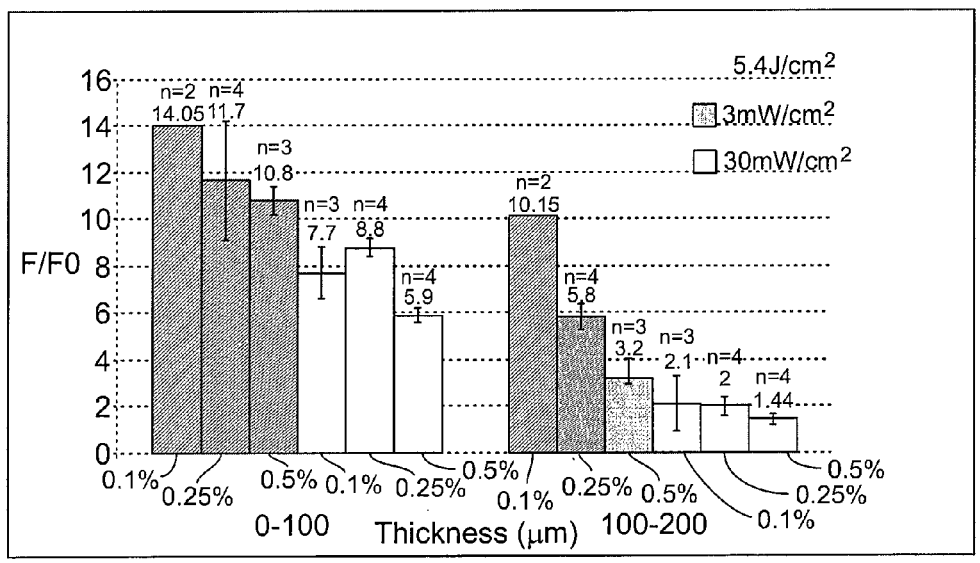
FIG. 4B illustrates a graph of relative fluorescence of cross-linked Riboflavin flaps at different Riboflavin concentrations and depths.

Fluorescence of the excised samples, which was a relative value to the non-cross-linked samples with the same thickness, is illustrated in FIG. 4B. It is shown that the corneal fluorescence after cross-linking (all samples were exposed to the same UVA dose, 5.4 J/cm$^2$) is greater for samples exposed to UVA for a longer duration with lower irradiance and lower concentration of Riboflavin. Corneal fluorescence is also greater at first 100 μm than at the next 100 μm in the cornea. The highest corneal fluorescence was observed at the first 100 μm for the sample that was soaked in 0.1% Riboflavin solution and irradiated at 3 mW/cm$^2$.

Example 3

Figure 5A:
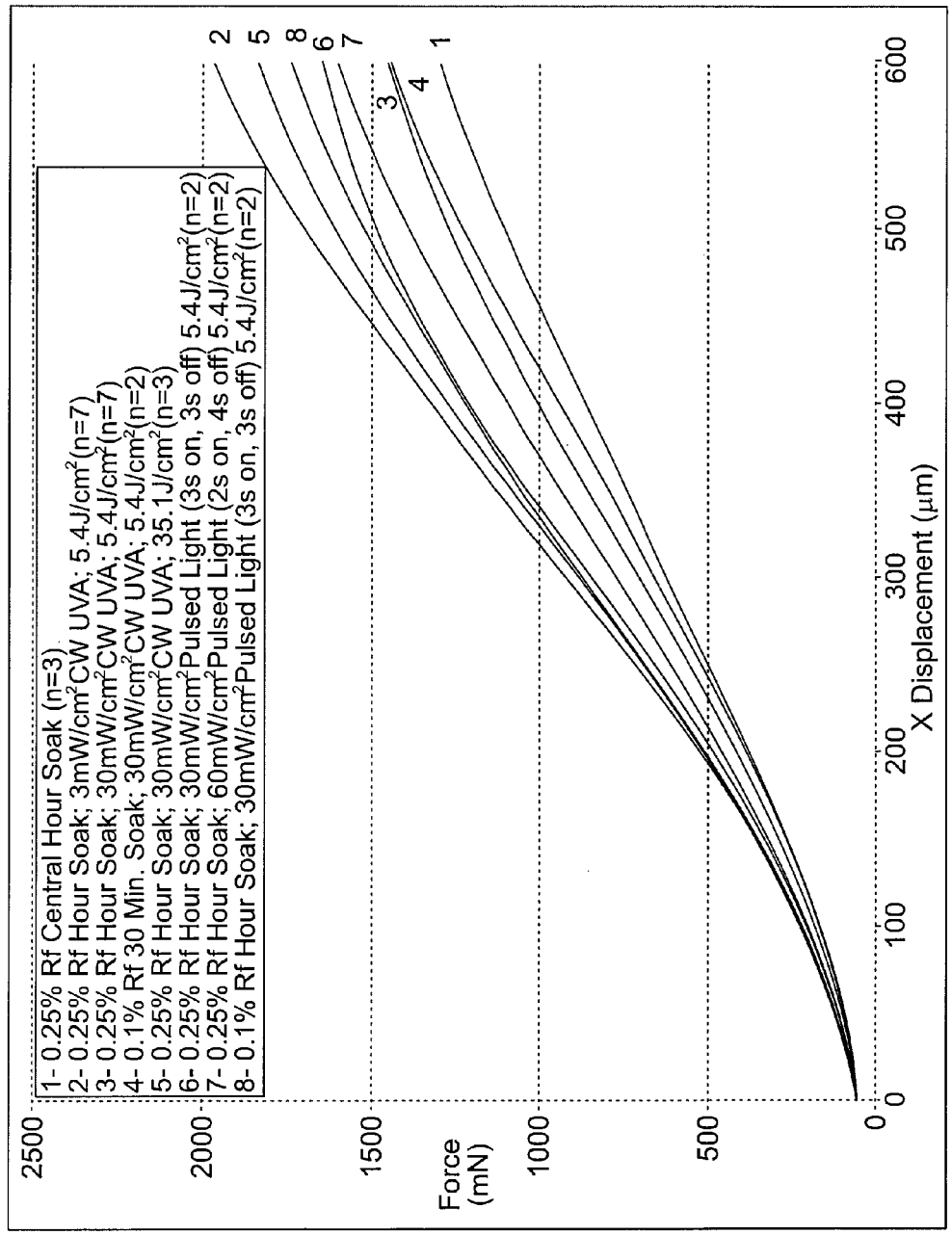
FIGS. 5A-5C illustrate graphs of force versus displacement curves for porcine cornea for various soak times and UVA illumination scenarios.
Figure 5B:
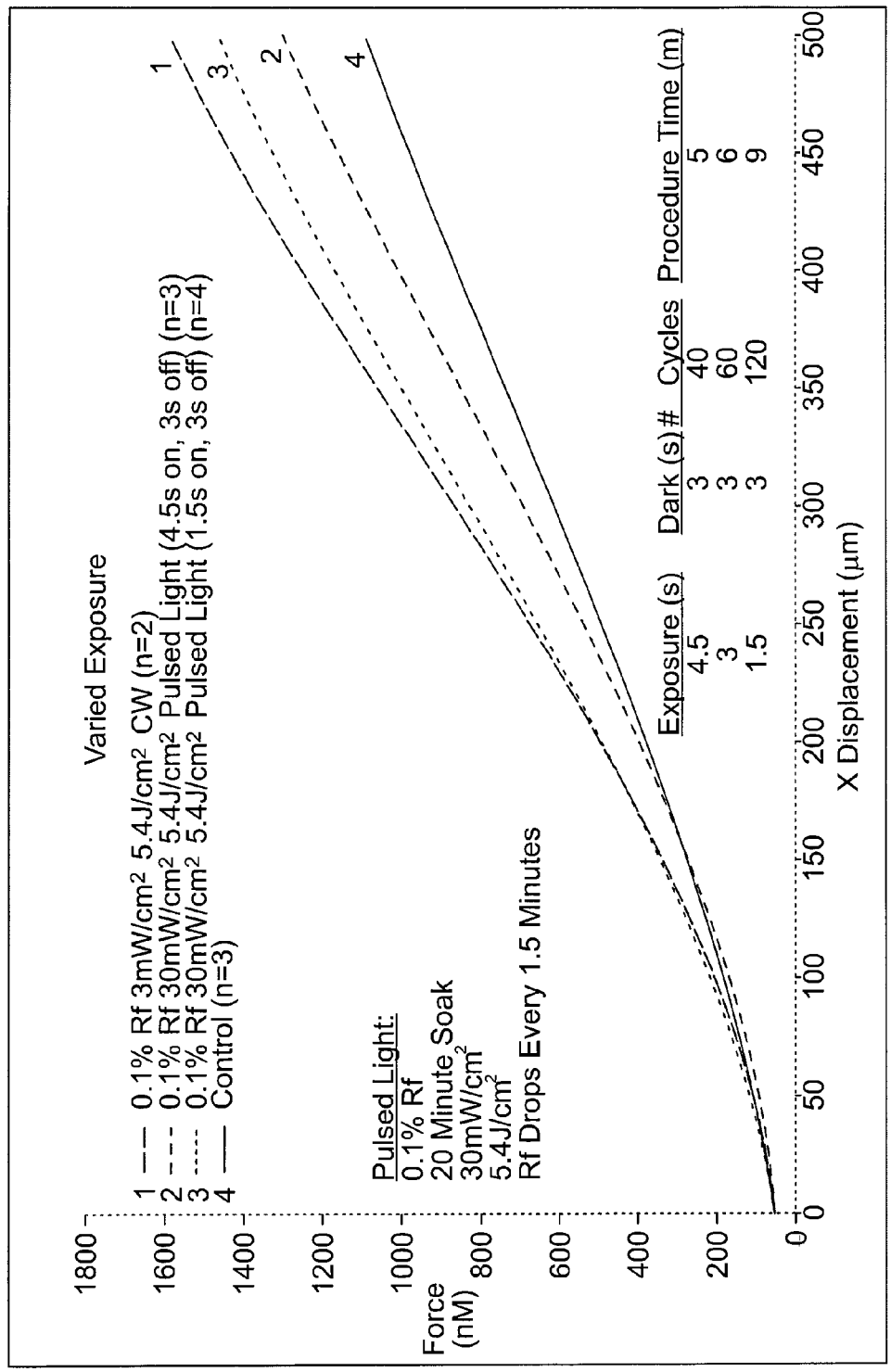
Figure 5C:
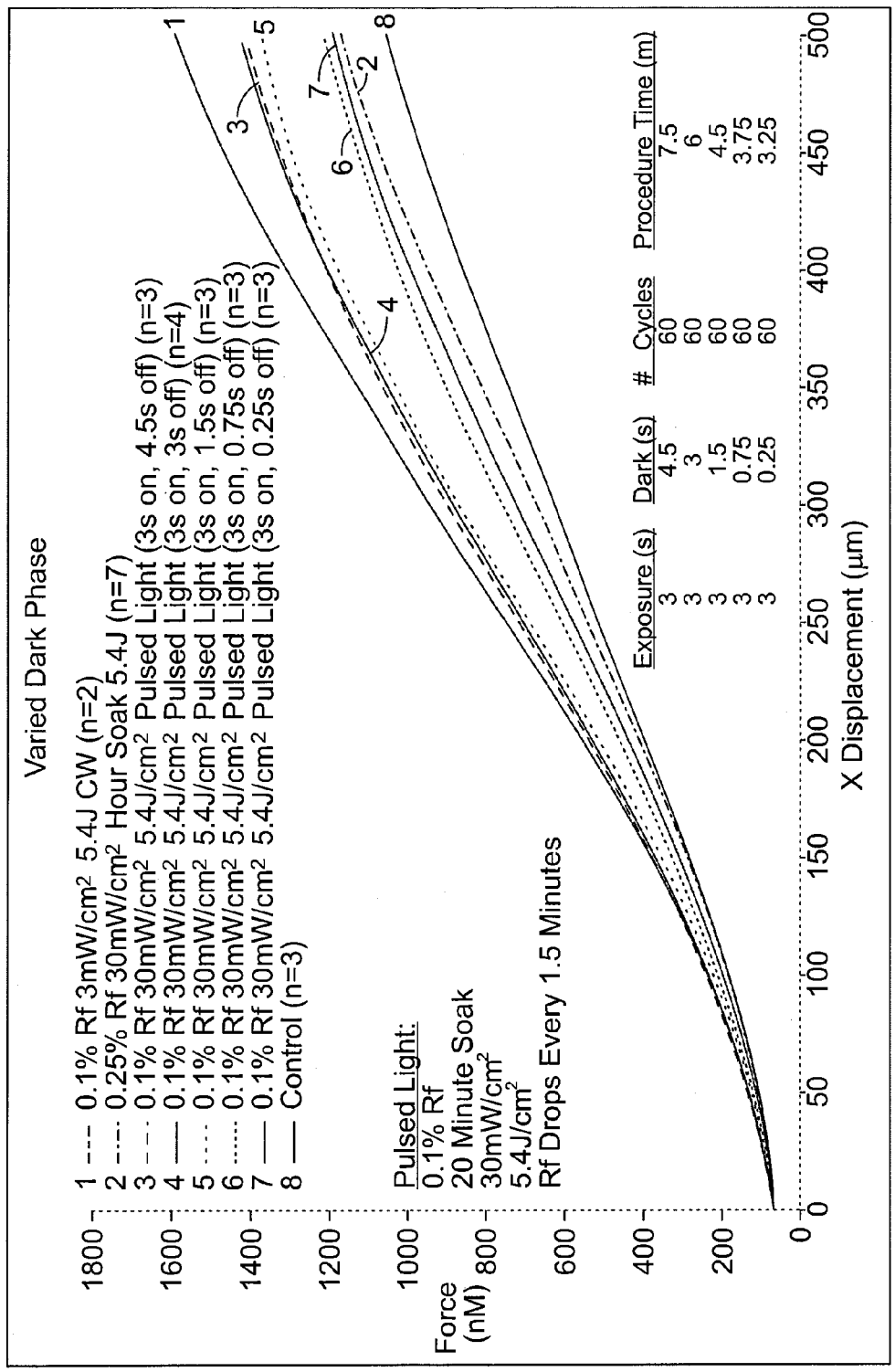

Upon arrival, porcine eyes have excess muscle tissue that was removed and placed in saline in the incubator (set to 37° C.) for 30 minutes. Eyes were then de-epithelialized and placed in a 0.1% Riboflavin solution for 20 minutes at 37° C. Eyes were removed from solution and physiological IOP was applied. Eyes were then placed under a UVA source and shutter system and irradiated according to the indicated protocol as shown in FIGS. 5A-5C. Riboflavin drops were applied every 1.5 minutes during UVA application. After being irradiated, the corneal thickness was measured with a pachymeter. The sample was then placed under the femto second laser and a ~200 μm flap was cut. The flap was positioned in a biaxial materials tester (CS-BIO TESTER 5000, CellScale, Waterloo, ON Canada) and stretched until failure. The sample was then rinsed with distilled water and frozen for future papain digestion and fluorescence analysis.

FIG. 5A illustrates force versus displacement curves for porcine cornea for various soak times and UVA illumination scenarios. FIG. 5A illustrates results of experiments that show dissimilar biomechanical stiffness of the 0.25% Riboflavin sample 2 irradiated with 3 mW/cm$^2$ continuous wave illumination vs. the sample 3 irradiated with 30 mW/cm$^2$ continuous wave illumination for a total 5.4 J/cm$^2$ dose delivered. The biomechanical stiffness of the 0.25% Riboflavin sample 3 irradiated with 30 mW/cm$^2$ continuous for a total 5.4 J/cm$^2$ dose delivered was similar to the biomechanical stiffness of the 0.1% Riboflavin sample 4 irradiated under the same conditions. The biomechanical stiffness of the 0.25% Riboflavin sample 6 irradiated with 30 mW/cm$^2$ pulsed light with a 3 seconds on/3 seconds off duty cycle was similar to the biomechanical stiffness of 0.25% Riboflavin sample 7 irradiated with 60 mW/cm$^2$ pulsed light with a 2 seconds on/4 seconds off duty cycle for a total 5.4 J/cm$^2$ dose delivered to each sample. The biomechanical stiffness of the 0.1% Riboflavin sample 8 irradiated with 30 mW/cm$^2$ pulsed light with a 3 seconds on/3 seconds off duty cycle was higher than both the samples 6 and 7. The biomechanical stiffness of the Riboflavin sample 5 irradiated with 30 mW/cm$^2$ continuous wave illumination for a total 35.1 J/cm$^2$ dose delivered was higher than that for samples 6, 7, 3, 4, and 1 (control sample with 0.25% Riboflavin concentration) and lower than that for sample 2. Sample 4 was soaked with Riboflavin for 30 minutes, while all the other samples were soaked with Riboflavin for 1 hour.

FIG. 5A illustrates the effect of varying different parameters on corneal cross-linking Different parameters—irradiance, continuous wave vs. pulsed illumination, on/off duty cycle of pulsed light illumination, Riboflavin concentration, and other parameters—all have an effect on biomechanical stiffness.

A DMD may be used for illumination. With the DMD one can perform topography guided cross-linking as described, for example, in U.S. patent application Ser. No. 13/438,705, filed Apr. 3, 2012, and U.S. patent application Ser. No. 13/051,699, filed Mar. 18, 2011, the contents of which are incorporated entirely herein by reference. The algorithms associated with the topography may be created using several different spatial and temporal irradiance and dose profiles.

These spatial and temporal dose profiles may be created using continuous wave illumination but may also be modulated via pulsed illumination by pulsing the illumination source under varying frequency and duty cycle regimes as described above. Or, the DMD may be able to modulate different frequencies and duty cycles on a pixel by pixel basis to give ultimate flexibility using continuous wave illumination. In a third alternative, both pulsed illumination and modulated DMD frequency and duty cycle combinations may be combined. This allows for specific amounts of spatially determined corneal cross-linking. This spatially determined cross-linking may be combined with dosimetry, interferometry, optical coherence tomography (OCT), corneal topography, etc., for real-time modulated corneal cross-linking Additionally, the pre-clinical patient information may be combined with finite element biomechanical computer modeling to create patient specific pre-treatment plans.

Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea to allow for various amounts of refractive correction. These refractive corrections may include combinations of myopia, hyperopia, astigmatism, irregular astigmatism, presbyopia and complex corneal refractive surface corrections because of ophthalmic conditions such as keratoconus, pellucid marginal disease, post-lasik ectasia, and other conditions of corneal biomechanical alteration/degeneration, etc.

A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz as described above.

Thus, applying pulsed light instead of continuous wave illumination has an effect on biomechanical stiffness. This is yet one more parameter that may be altered in optimizing cross-linking.

Flicker vertigo, sometimes called the Bucha effect, is an imbalance in brain-cell activity caused by exposure to low-frequency flickering (or flashing) of a relatively bright light. It is a disorientation-, vertigo-, and nausea-inducing effect of a strobe light flashing at 1 Hz to 20 Hz, which corresponds approximately to the frequency of human brainwaves. The effects are similar to seizures caused by epilepsy (particularly, photosensitive epilepsy), but are not restricted to people with histories of epilepsy. In the United States, websites provided by federal agencies are governed by section 508 of the Rehabilitation Act. The Act says that pages shall be designed to avoid causing the screen to flicker with a frequency between 2 Hz and 55 Hz. The 508 regulations are currently being updated and are expected to use the same criteria as WCAG 2.0 when completed. (Section 508 Subpart B—Technical Standards §1194.21 Software applications and operating systems.—(k) Software shall not use flashing or blinking text, objects, or other elements having a flash or blink frequency between 2 Hz and 55 Hz.) Photosensitive seizures are those triggered by either flashing or flickering lights, or rapidly changing geometric shapes or patterns. Many people with epilepsy are unaware that they are sensitive to certain kinds of lights or flickering patterns until they have a seizure. Less than 5% of those who suffer from epilepsy are photosensitive. This means that approximately one in 4,000 individuals suffer from this—which corresponds to less than 100,000 in the U.S. population. The characteristics of each individual's susceptibility are unique. A certain photosensitive individual may not be susceptible to a given light display at all. Still it is clear that every public display of lights can expect to regularly affect photosensitive epileptics—thus, a high degree of diligence is due the effort to eliminate displays which may trigger seizures. It is well documented that the range of 15 to 20 Hz is of greatest concern, however some individuals are susceptible to flashing lights as slow as 5 Hz and some as high as 84 Hz.

FIG. 5B illustrates force versus displacement curves for samples of porcine cornea irradiated with pulsed light having various exposure times, as well as a curve for a sample irradiated with continuous wave illumination, and a curve for a control sample. All the samples that were irradiated with pulsed light had a 0.1% Riboflavin concentration and were irradiated with 30 mW/cm$^2$ pulsed light with a 3 seconds off cycle and a varied exposure ("on") cycle. The sample 2 having a 4.5 second exposure cycles had slightly lower biomechanical stiffness than samples 3 or 1. Thus, the duration of the exposure cycle affects the amount of corneal stiffening at the same irradiance and dark phase duration. Therefore, aspects of the present disclosure affect the displacement per unit force ratio. This is yet one more parameter that may be altered in optimizing cross-linking.

FIG. 5C illustrates force versus displacement curves for samples of porcine cornea illuminated with pulsed light having varied dark phase durations, as well as curves for samples irradiated with continuous illumination, and a curve for a control sample. The sample 1 having 0.1% Riboflavin concentration irradiated with 3 mW/cm$^2$ continuous wave illumination had the highest biomechanical stiffness. The samples having 0.1% Riboflavin concentration that were irradiated with 30 mW/cm$^2$ pulsed light with 3 seconds on/4.5 seconds off (sample 2) and with 3 seconds on/3 seconds off (sample 4) duty cycles had slightly lower biomechanical stiffness, followed by, in descending order, samples irradiated with 30 mW/cm$^2$ pulsed light with 3 seconds on cycles and 1.5 (sample 5), 0.75 (sample 6), and 0.25 (sample 7) seconds off (dark phase) cycles. The sample 2 having 0.25% Riboflavin concentration irradiated with 3 mW/cm$^2$ continuous wave illumination had the lowest biomechanical stiffness out of samples 1 and 3-7. Thus, the duration of the dark phase affects the amount of corneal stiffening even at the same irradiance and exposure duration. This is yet one more parameter that may be altered in optimizing cross-linking.

The graphs in FIGS. 5A-5C show that varying different parameters—applying pulsed instead of continuous wave illumination, varying on/off duty cycles, irradiance, dose, Riboflavin concentration, and soak times—all have an effect on biomechanical stiffness. These parameters may be modified in such a way as to achieve an optimum or desired amount of corneal stiffness anywhere on or within the cornea.

In a corroborating experiment, porcine eyes were de-epithelialized and placed in the 0.1% Riboflavin solution for 20 minutes. Eyes were removed from solution and physiological IOP was applied. A flap was cut using a femto second laser and an $O_2$ sensor was placed under the flap. UVA illumination was administered as indicated and Riboflavin drops were applied every 90 seconds for the duration of the dose delivered. After cross-linking the flap using the pulsed light dosing, the flap was removed and tested mechanically as described above.

Results from the $O_2$ sensor (FIG. 2B) show that under pulsed light irradiation, oxygen slightly increases cyclically with the duty cycle of the pulsed light. It appears that locally available $H_2O_2$ during the dark phase of the pulsed light cycle does indeed supply small amounts of oxygen back into the system capable of allowing reactivation of reduced Riboflavin and its conversion into Deuteroflavin ($Rf_{ox}$) as described above. Oxygen diffusion from the surface by itself takes much longer to account for these observations.

Example 4—Fluorescence of Samples Irradiated with Continuous Wave Illumination Versus Pulsed Light Illumination In another corroborating experiment porcine whole globes (SiouxPreme Packing Co., Sioux City, Iowa; shipped in saline solution packed in ice) were warmed to room temperature (25 C). The corneas were then de-epithelialized with a dulled scalpel blade and 0.1, Riboflavin solution in 0.9% saline was applied to the top of each cornea during 20 minutes before cross-linking in an incubator. Corneas were pan-corneally irradiated with a top hat beam (3% root mean square) for a determined amount of time with 365-nm light source (UV LED NCSU033B[T]; Nichia Co., Tokushima, Japan) at the chosen irradiance of 30 mW/cm$^2$ with either continuous wave illumination or pulsed illumination 3 seconds on/3 Seconds off. Corneal flaps (200 μm thick) were excised from the eyes with aid of Intralase femtosecond laser (Abbott Medical Optics, Santa Ana, Calif.). The average thickness of the corneal flaps was calculated as a difference between the measurements before and after the excision from the eyes with an ultrasonic Pachymeter (DGH Technology, Exton, Pa.).

The flaps were washed with distilled water until Riboflavin in the washing waters was not detectable by absorbance measurement at 455 nm (Thermo Scientific Evolution 300/600 UV-Vis Spectrophotometer, Thermo Fisher Scientific, Waltham, Mass.). The flaps then were dried in vacuum until the weight change became less than 10% (Rotary vane vacuum pump RV3 A652-01-903, BOC Edwards, West Sussex, UK). Each flap (1 mg) was digested for 2 h at 65° C. with 2.5 units/ml of papain (from Papaya latex, Sigma) in 0.5 ml of papain buffer [1×PBS (pH 7.4), 2 mM L-cysteine and 2 mM EDTA]. Papain digests were centrifuged for 30 seconds at 2200×G (Mini centrifuge 05-090-100, Fisher Scientific), diluted 3 times with 1×PBS solution and fluorescence of the solutions was measured with excitation of $\lambda_{ex}=360$ nm in a QM-40 Spectrofluorometer (Photon Technology Int., London, Ontario, Canada).

The fluorescence of the papain buffer was taken into account by measuring fluorescence in the absence of tissue and subtracting this value from the fluorescence of the samples. The results seen below corroborate that the amount of fluorescence seen which is directly related to the amount of cross-linking is greater for the pulsed vs. continuous wave illumination in nearly the same proportion as the biomechanical measurements taken of the same flaps.

Figure 6:
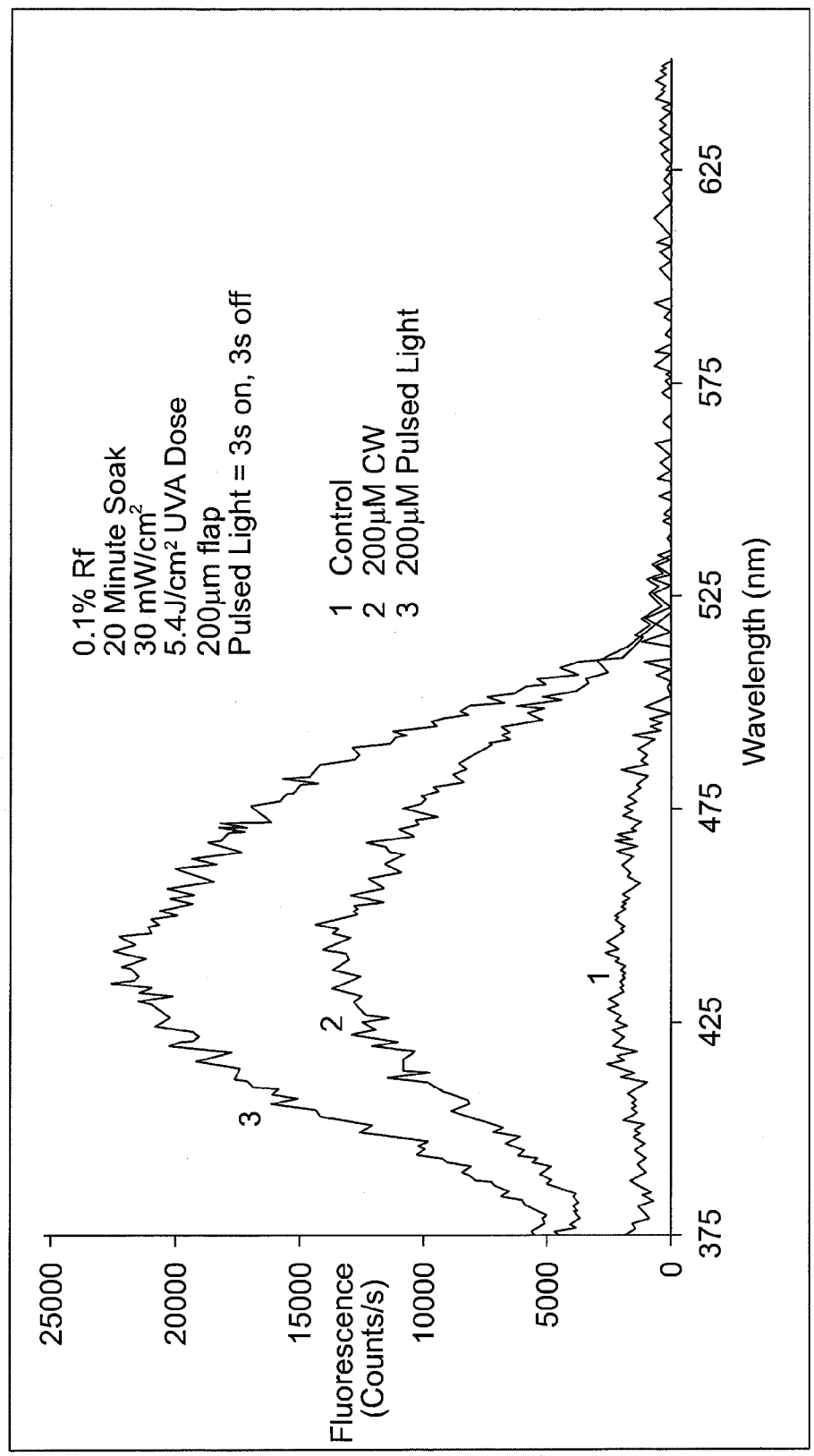
FIG. 6 illustrates a graph of fluorescence versus wavelength for porcine cornea 200 μm flaps for various UVA illumination scenarios.

Referring now to FIG. 6, a graph of fluorescence versus wavelength curves is shown. At 455 nm, fluorescence was the highest—about 20,000 counts/s—for the sample irradiated with 30 mW/cm$^2$ pulsed light illumination with a 3 seconds on/3 seconds off cycle. The fluorescence for the sample irradiated with 30 mW/cm$^2$ continuous illumination was about 40% less, or about 12000 counts/s. This is yet another example demonstrating that applying pulsed light illumination as opposed to continuous wave illumination affects cross-linking in the cornea.

Example 5—Cross-Linking Measured by Fluorescence of Digested Corneal Flaps at 450 nm Pig eyes from an abattoir (SiouxPreme, Sioux City, Iowa) were rinsed in saline. Eyes were cleaned and the epithelium was removed. Eyes were placed on a stand in the middle of a large beaker filled part way with water with a tube bubbling compressed oxygen into the water. The oxygen was turned on at certain times during the experiment to create a humid oxygenated environment for the eye. Eyes were soaked for 20 minutes with 0.1% Riboflavin, dH$_2$O solution in an incubator set at 37° C. by using a rubber ring to hold the solution on top. Corneas were pan-corneally irradiated with a top hat beam (3% root mean square) for a determined amount of time and irradiance (3 minutes CW at 30 mW/cm$^2$ with one drop of solution added every 30 seconds, or 30 minutes CW at 3 mW/cm$^2$ with one drop of solution added every minute, or 9 minutes for pulsed light—1.5 seconds on/3 seconds off—using a shutter system (Lambda SC Smart Shutter, Sutter Instrument, Novato, Calif.) at 30 mW/cm$^2$ with one drop of solution added every minute) with a 365-nm light source (UV LED NCSU033B [T]; Nichia Co., Tokushima, Japan). The irradiance was measured with a power sensor (model PD-300-UV; Ophir, Inc., Jerusalem, Israel) at the corneal surface.

Corneal flaps (approximately 380 μm thick) were excised from the eyes with aid of Intralase femtosecond laser (Abbott Medical Optics, Santa Ana, Calif.). The average thickness of the corneal flaps was calculated as a difference between the measurements before and after the excision from the eyes with an ultrasonic Pachymeter (DGH Technology, Exton, Pa.). The flaps were washed with distilled water 15 times and then dried in a vacuum until the weight change became less than 10% (Rotary vane vacuum pump RV3 A652-01-903, BOC Edwards, West Sussex, UK). Each flap (2 mg) was digested for 2.5 h at 65° C. with 2.5 units/ml of papain (from Papaya latex, Sigma) in 1 ml of papain buffer [1×PBS (pH 7.4), 2 mM L-cysteine and 2 mM EDTA]. Papain digests were centrifuged for 20 seconds at 2200×G (Mini centrifuge 05-090-100, Fisher Scientific), diluted 0.5 times with 1×PBS solution (in other words, 0.5 mL of PBS was added to 1 mL of solution) and fluorescence of the solutions was measured with excitation of $\lambda_{ex}$=360 nm in a QM-40 Spectrofluorometer (Photon Technology Int., London, Ontario, Canada). The fluorescence of the papain buffer was taken into account by measuring fluorescence in the absence of tissue and subtracting this value from the fluorescence of the samples.

Figure 7A:
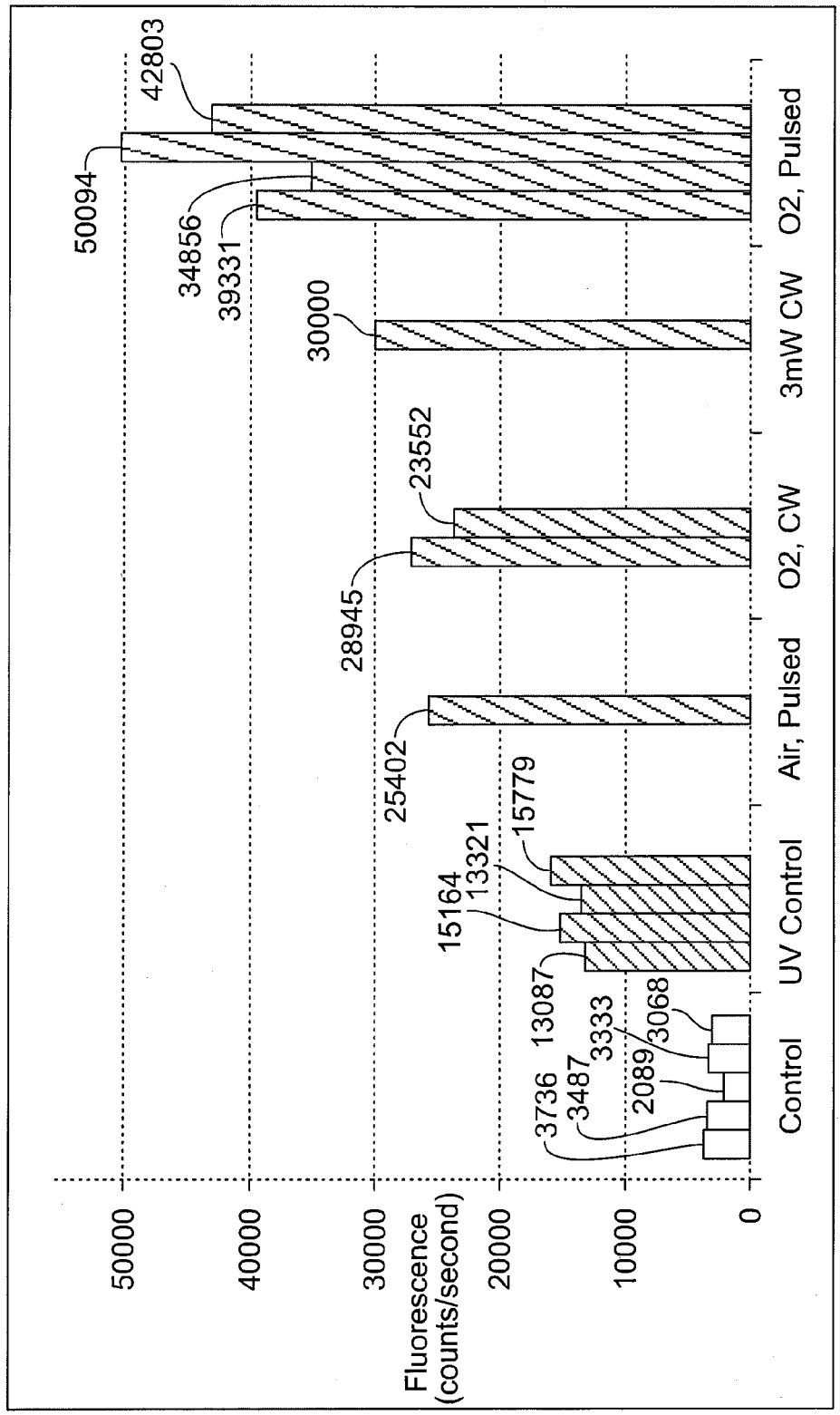
FIG. 7A illustrates a graph of cross-linking measured by fluorescence of the digested corneal flap at 450 nm for various UVA illumination scenarios.

FIG. 7A illustrates a graph of the amount of cross-linking measured by fluorescence of the digested corneal flaps at 450 nm. Eyes were de-epithelized, soaked for 20 minutes with 0.1% Riboflavin, put in a regular air environment or a humid oxygenated environment, and illuminated with 30 mW/cm$^2$ or 3 mW/cm$^2$ of UV light for 3 minutes CW with one drop of solution every 30 seconds, or 30 minutes CW with one drop of solution every minute, or 9 minutes pulsed (1.5 seconds on/3 seconds off) with one drop of solution every minute. The following treatments shown in Table 2 below were applied to each of the samples shown in FIG. 7A:

TABLE 2

Treatment Conditions for the Samples Shown in FIG. 7A

| Sample | Treatment |
| --- | --- |
| Control | After being soaked, corneal flaps were cut at approximately 380 μm. |
| UV Control | Eyes were illuminated with 30 mW/cm$^2$ CW of UV light for 3 minutes. |
| Air, Pulsed Light | Eyes were illuminated with 30 mW/cm$^2$ pulsed UV light (1.5 seconds on/3 seconds off) for 9 minutes. |
| O$_2$, CW | Eyes were illuminated with 30 mW CW/cm$^2$ of UV light for 3 minutes with oxygen always on during UV exposure and soak. |
| 3 mW CW | Eyes were illuminated with 3 mW/cm$^2$ CW of UV light for 30 minutes. |
| O$_2$, Pulsed Light | Eyes were illuminated with 30 mW/cm$^2$ of pulsed UV light (1.5 seconds on/3 seconds off) for 9 minutes with oxygen on during soak and UV exposure. |

As shown in FIG. 7A, a humid oxygenated environment with pulsed UV light greatly increases the amount of cross-linking taking place in the cornea. Applying a combination of Riboflavin and ultraviolet (UV) light sterilizes a surface of the cornea. The Riboflavin acts as a photosensitizer that increases the absorption of UV light. The resulting absorption of UV light can induce DNA and RNA lesions, and as a result, is effective in killing viruses, bacteria, and other pathogens in the field.

A humid oxygen environment and pulsing UV light increase the amount of cross-linking to a certain degree when done separately, while they increase the amount of cross-linking to a significantly greater extent when done in conjunction. Increased cross-linking involves creation of an increased number of radicals. Radicals help to eliminate harmful bacteria present in the eye. Accordingly, a humid oxygenated environment and pulsing UV light result in more efficient elimination of viruses, bacteria, and other pathogens in the cornea, creating a sterile environment while minimizing any damage or other unwanted effects in the tissue. This is yet another example demonstrating that applying pulsed light illumination as opposed to continuous wave illumination affects the amount of cross-linking in the cornea.

Figure 7B:
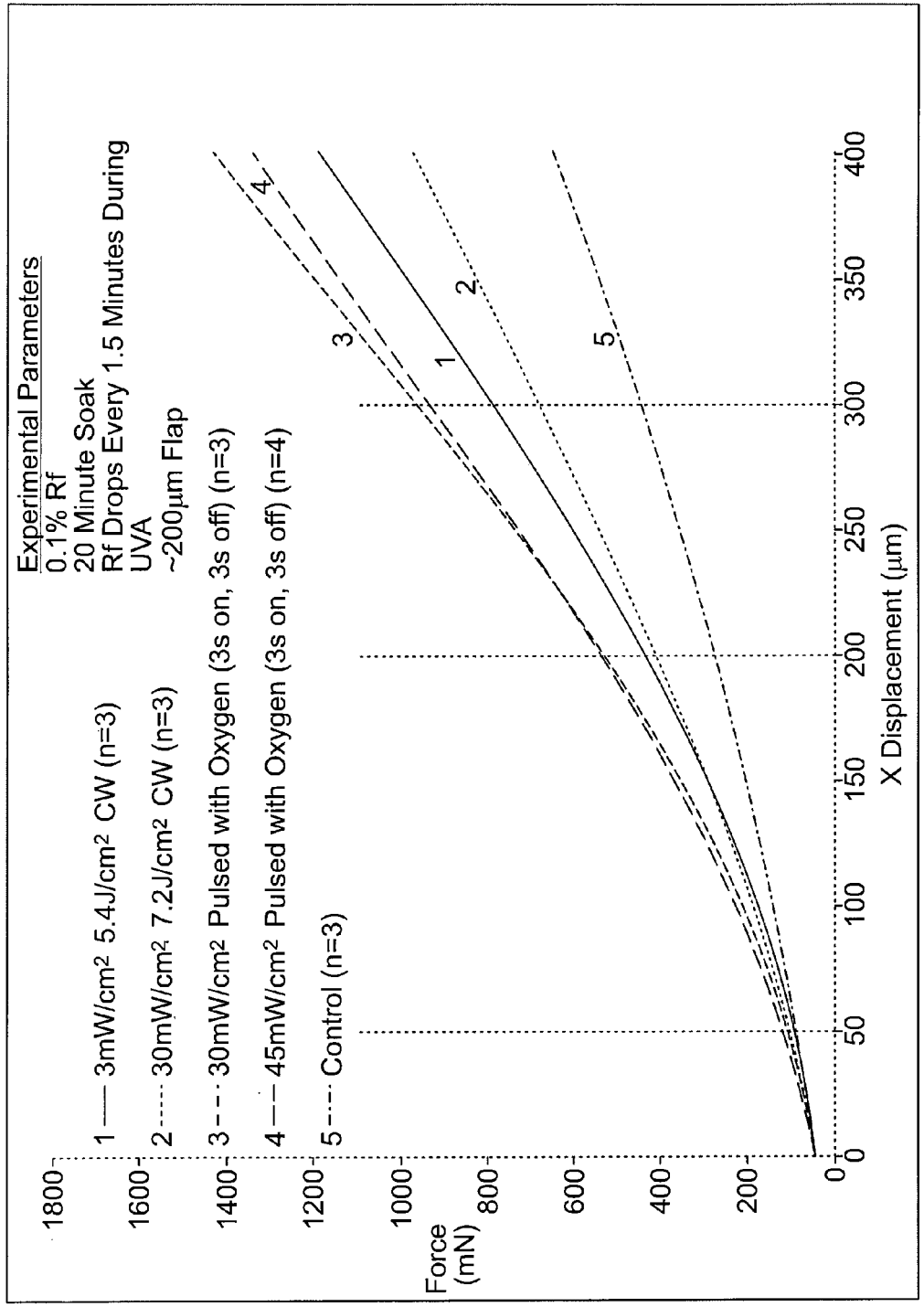
FIG. 7B illustrates a graph of force versus displacement curve for porcine cornea for various UVA illumination scenarios.

FIG. 7B illustrates force versus displacement curves for samples of porcine cornea illuminated with pulsed light of irradiance with oxygen, as well as curves for samples irradiated with continuous illumination, and a curve for a control sample. The sample 3 irradiated with 30 mW/cm$^2$ pulsed light illumination with oxygen and a 3 seconds on/3 seconds off duty cycle had the highest biomechanical stiffness, followed by sample 4 irradiated with 45 mW/cm$^2$ pulsed light illumination with oxygen and an identical on/off duty cycle. The samples irradiated with 3 mW/cm$^2$ and 30 mW/cm$^2$ continuous wave illumination had lower biomechanical stiffness, followed by the control sample. Thus, the addition of oxygen affects the amount of corneal stiffening even at the same on/off duty cycle. This is yet one more parameter that may be altered in optimizing cross-linking.

Figure 8A:
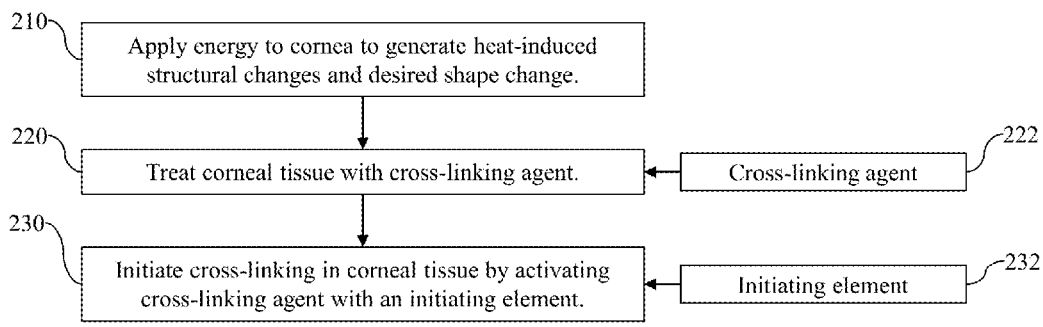
FIG. 8A illustrates an example approach for stabilizing or strengthening corneal tissue by applying a cross-linking agent according to aspects of the present invention.

It is contemplated that oxygen may be applied during the cross-linking treatments in a number of different ways. For example, referring to FIG. 8A, a treatment, such as thermokeratoplasty or LASIK surgery, is applied in step 210 to generate structural changes in the cornea and produce a desired shape change. In step 220, the corneal tissue is treated with a cross-linking agent 222. The cross-linking agent may be applied directly on the treated tissue and/or in areas around the treated tissue. In some embodiments, the cross-linking agent may be an ophthalmic solution that is broadly delivered by a dropper, syringe, or the like. Alternatively, the cross-linking agent may be selectively applied as an ophthalmic ointment with an appropriate ointment applicator. The cross-linking agent 222 is then activated in step 230 with an initiating element 232. Activation of the cross-linking agent 222, for example, may be triggered thermally by the application of microwaves or light from a corresponding energy or light source. The resulting cross-linking between collagen fibrils provides resistance to changes in corneal structure.

Figure 8B:
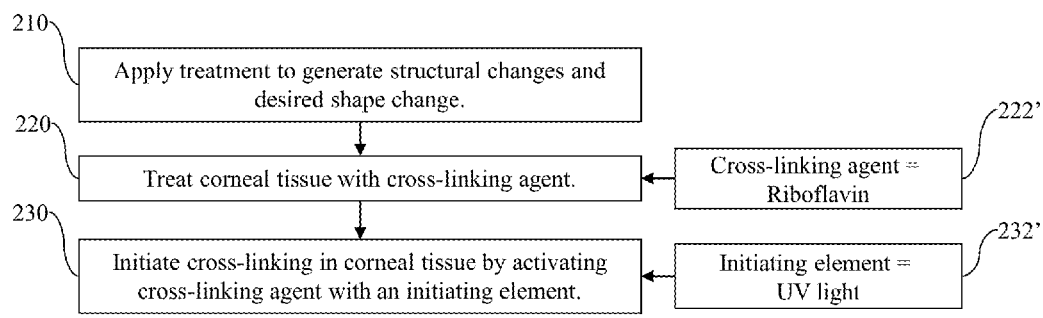
FIG. 8B illustrates an example approach for stabilizing or strengthening corneal tissue by applying Riboflavin as a cross-linking agent according to aspects of the present invention.

As FIG. 8B shows further, Riboflavin is applied as a cross-linking agent 222' to the corneal tissue in step 220. In addition, light from an UV light source may be applied as an initiating element 232' in step 230 to initiate cross-linking in the corneal areas treated with Riboflavin. Specifically, the UV light initiates cross-linking activity by causing the applied Riboflavin to release reactive oxygen radicals in the corneal tissue. As explained above, the Riboflavin acts as a sensitizer to convert $O_2$ into singlet oxygen which causes cross-linking within the corneal tissue.

In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved.

Figure 9A:
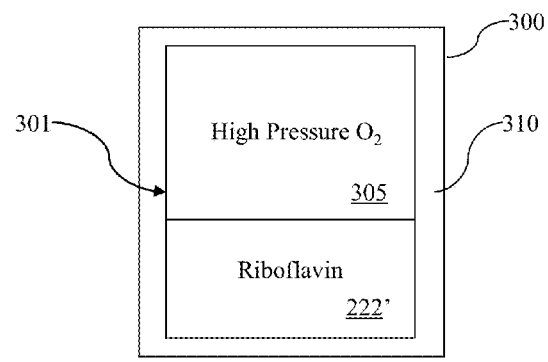
FIG. 9A illustrates an example device that may be employed to supersaturate a cross-linking agent with $O_2$ according to aspects of the present invention.
Figure 9B:
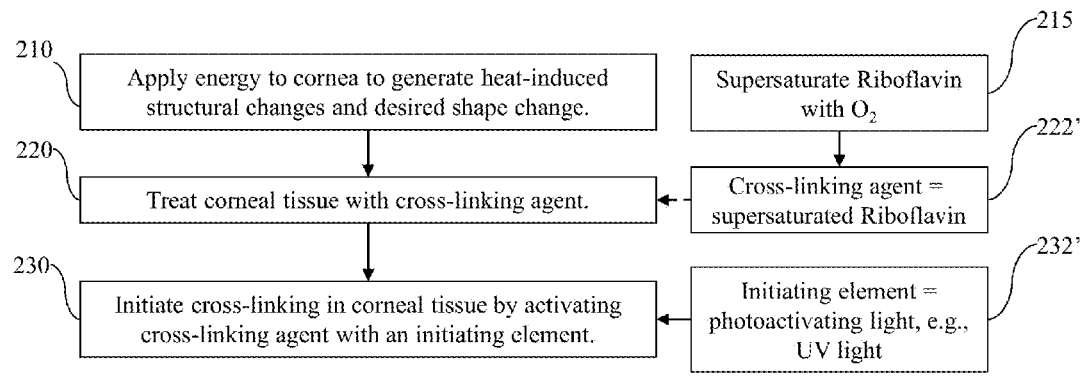
FIG. 9B illustrates an example approach for stabilizing or strengthening corneal tissue by applying supersaturated Riboflavin as a cross-linking agent according to aspects of the present invention.

An approach according to aspects of the present invention involves supersaturating the Riboflavin with $O_2$. Thus, when the Riboflavin is applied to the eye, a higher concentration of $O_2$ is delivered directly into the cornea with the Riboflavin and affects the conversion of $O_2$ into singlet oxygen when the Riboflavin is exposed to the photoactivating light. As illustrated in FIG. 9A, the Riboflavin 222' may be stored in a closed vessel, e.g., a vial, 300 under increased $O_2$ pressure 305. The increased $O_2$ pressure 305 results in a higher equilibrium concentration of $O_2$ in the Riboflavin 222'. The walls 310 of the vessel 300 are preferably opaque or otherwise prevent visible, UV, or other light from entering the vessel interior 301 to minimize the degradation of the Riboflavin 222'. Accordingly, referring to FIG. 9B, the step 215 supersaturates the Riboflavin 222' with $O_2$ so that a supersaturated Riboflavin 222' is applied in step 220.

Figure 10A:
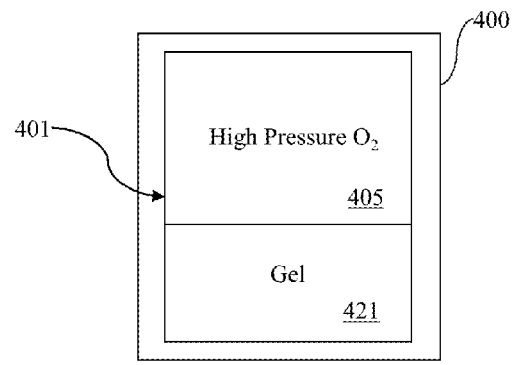
FIG. 10A illustrates an example device that may be employed to supersaturate a carrier gel with $O_2$ according to aspects of the present invention.

According to other aspects of the present invention, rather than supersaturating the Riboflavin 222' with $O_2$, another substance, such as a gel (e.g., a methylcellulose gel), may be saturated or supersaturated with $O_2$. As illustrated in FIG. 10A, a gel 421 may be stored in an interior 401 of a closed vessel, e.g., a vial, 400 under increased $O_2$ pressure 405. The increased $O_2$ pressure 405 results in a higher equilibrium concentration of $O_2$ in the gel 421. The gel can then act as a carrier for $O_2$.

Figure 10B:
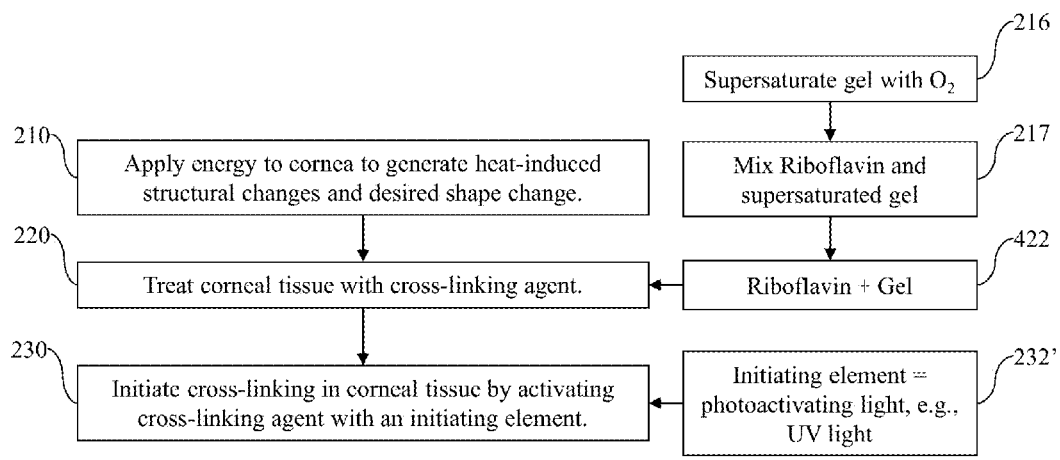
FIG. 10B illustrates an example approach for stabilizing or strengthening corneal tissue by mixing Riboflavin with a gel supersaturated with $O_2$ according to aspects of the present invention.
Figure 10C:
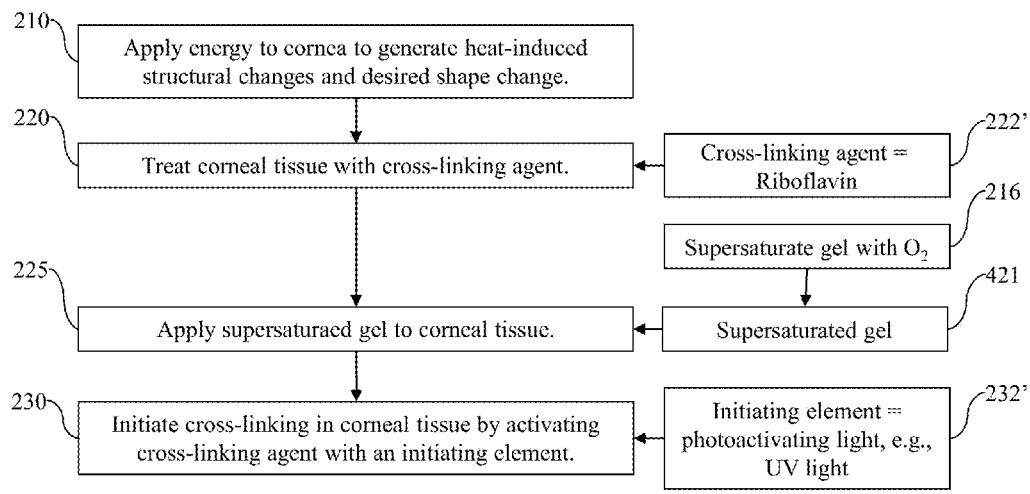
FIG. 10C illustrates an example approach for stabilizing or strengthening corneal tissue by applying a gel supersaturated with $O_2$ according to aspects of the present invention.

Referring to FIG. 10B, step 216 saturates a gel 421 with $O_2$, and step 217 mixes the supersaturated gel 421 with the Riboflavin 222', so that a mixture 422 containing the Riboflavin 222' and the supersaturated gel 421 is applied in step 220. Alternatively, referring to FIG. 10C, step 216 saturates a gel 421 with $O_2$, and step 225 applies the gel 421 to the cornea after the Riboflavin 222' has been applied to the cornea. In both FIGS. 10A and 10B, the gel 421 increases the presence of $O_2$ when the Riboflavin 222' is activated with the UV light.

According to additional aspects of the present invention, a steady state of $O_2$ may be maintained at the surface of the cornea to expose the cornea to a selected amount of $O_2$ and cause $O_2$ to enter the cornea. The photoactivating light can then be applied to a cornea with the desired $O_2$ content.

Figure 11A:
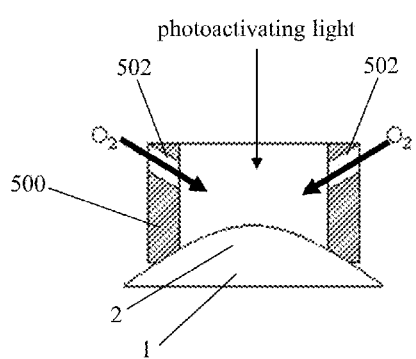
FIG. 11A illustrates an example device that may be employed maintain a steady state of $O_2$ above the eye to expose the cornea to higher concentrations of $O_2$ according to aspects of the present invention.

As shown in FIG. 11A, a ring 500 is placed on the eye 1 to supply $O_2$ to the cornea 2 during irradiation. The ring 500 includes one or more ports 502 that direct a steady flow of $O_2$ to the cornea 2, which has been treated by Riboflavin. The flow applies $O_2$ at high pressure against the cornea 2, so that more $O_2$ is available during the irradiation of the Riboflavin in the corneal tissue. The ring 500 may optionally be held in place by suction.

Figure 11B:
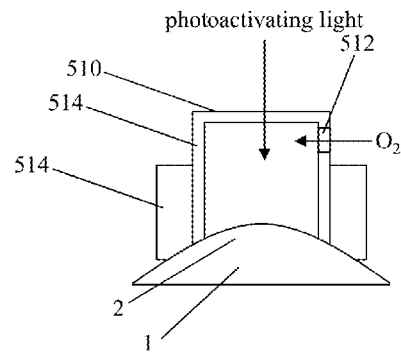
FIG. 11B illustrates another example device that may be employed to maintain a steady state of $O_2$ above the eye to expose the cornea to higher concentrations of $O_2$ according to aspects of the present invention.

As FIG. 11B illustrates, in another embodiment, an enclosure 510 receiving a supply of $O_2$ through a port 512 is placed on the eye to establish a steady state of $O_2$. The enclosure 510 may be held in place by a suction ring 512. As shown in FIG. 11B, the enclosure 510 may be a cup-like structure. The enclosure 510 maintains the $O_2$ at a higher pressure, e.g., higher than ambient, against the surface of the cornea 2. The concentration of $O_2$ within the enclosure 510 and above the surface of the cornea 2 can approach 100%. The $O_2$ within the enclosure 510 makes more $O_2$ to be available for the irradiation of the Riboflavin in the corneal tissue. At least a portion of the walls 514 of the enclosure 510 may be translucent to allow photoactivating light to pass through the enclosure 510 to irradiate the cornea 2 and activate the Riboflavin applied to the cornea 2. Alternatively, the light source may be disposed within the enclosure. The enclosure 510 may also include a valve that allows the gas to be released.

Figure 11C:
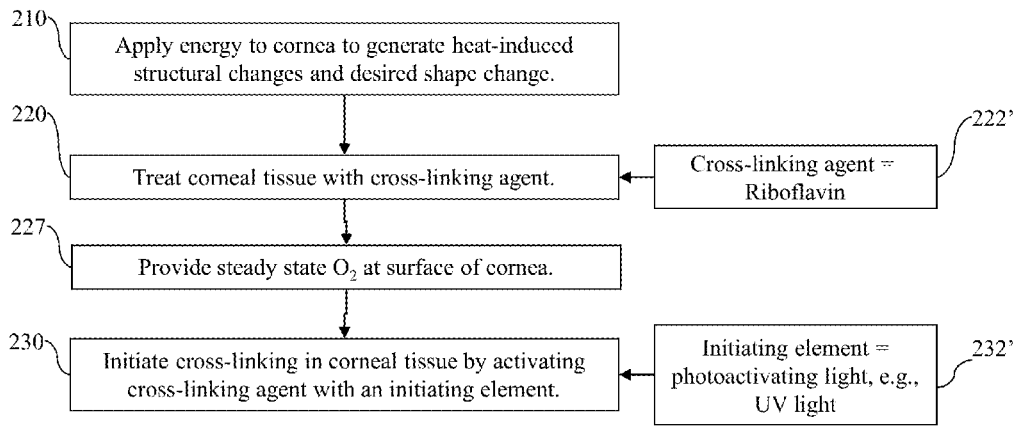
FIG. 11C illustrates an example approach for stabilizing or strengthening corneal tissue by applying a state of $O_2$ above the eye to expose the cornea to higher concentrations of $O_2$.

Accordingly, referring to FIG. 11C, step 227 establishes a steady state of $O_2$ above the corneal surface before the photoactivating light 232' is applied in step 230 to initiate cross-linking with the Riboflavin 222'.

Figure 12:
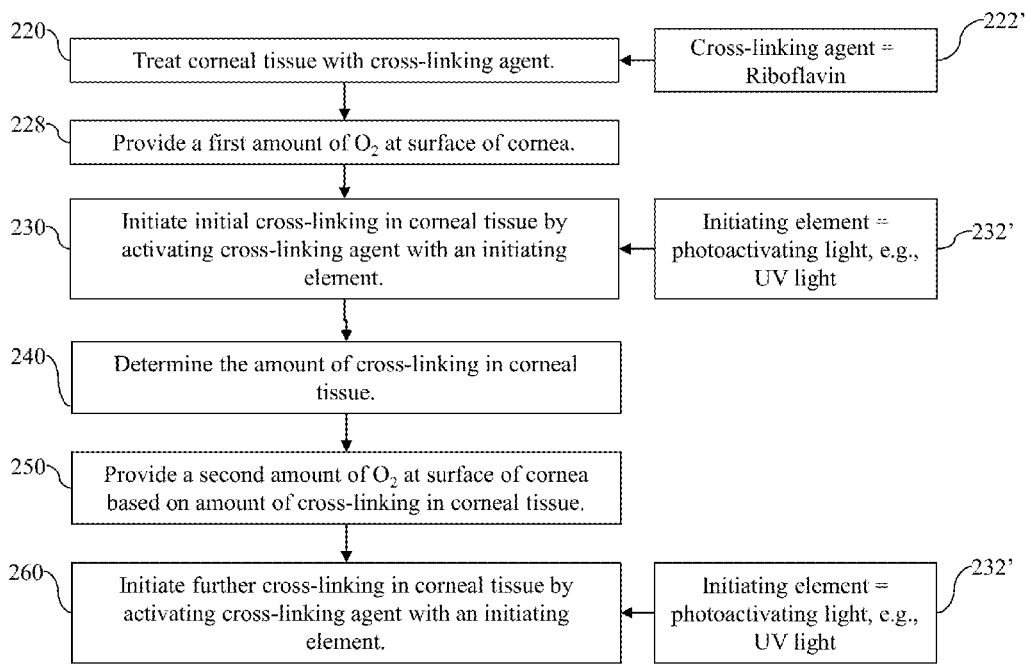
FIG. 12 illustrates an example approach for stabilizing or strengthening corneal tissue by monitoring cross-linking activity in real time and controlling the amount of $O_2$ exposure to achieve desired rates of cross-linking according to aspects of the present invention.

Referring to FIG. 12, the rate of cross-linking may be monitored in real time and the concentration of $O_2$ may be dynamically increased or decreased to achieve a desired amount of cross-linking. As FIG. 12 illustrates, corneal tissue is treated with Riboflavin 222' in step 220. In step 228, a first amount of $O_2$ is provided above the corneal surface to introduce $O_2$ to the corneal tissue and establish a first concentration of $O_2$ in the cornea during irradiation. The devices described with reference to FIGS. 11A and 11B may be employed to change the amount of $O_2$ is provided above the corneal surface. The Riboflavin 222' is then activated in step 230 with UV light 232'.

In step 240, the amount of cross-linking resulting from the activation of the Riboflavin 222' is monitored. One technique for monitoring the cross-linking employs polarimetry to measure corneal birefringence and to determine the structure of the corneal tissue. In particular, the technique measures the effects of cross-linking on corneal structure by applying polarized light to the corneal tissue. The corneal stroma is anisotropic and its index of refractions depends on direction. The cornea behaves like a curved biaxial crystal with the fast axis orthogonal to the corneal surface and the slow axis (or corneal polarization axis) tangential to the corneal surface. Accordingly, a light beam emerging from the living eye after a double pass through the ocular optics contains information on the polarization properties of the ocular structures (except optically inactive humours). The technique of using birefringence to monitor the structural changes resulting from cross-linking is described further in U.S. Provisional Patent Application No. 61/388,963, filed Oct. 1, 2010, the contents of which are entirely incorporated herein by reference. A controller, employing conventional computer hardware or similar processing hardware, can be used to monitor the amount of cross-linking. Such hardware may operate by reading and executing programmed instructions that are stored or fixed on computer-readable media, such as conventional computer disk. In addition to being coupled to monitoring hardware, the controller may be coupled to, and automatically control, the device(s) that provide the $O_2$ above the corneal surface.

Based on the information from the real time monitoring in step 240, step 250 provides a second amount of $O_2$ above the eye to introduce another amount of $O_2$ to the corneal tissue and expose the cornea to a second concentration of $O_2$ during irradiation with UV light 232' in step 260. Steps 240, 250, and 260 may be repeated any number of times to change the concentration of $O_2$ during irradiation to control the rate of cross-linking dynamically.

The first amount of $O_2$ in step 228 may be greater than the second amount of $O_2$ in step 250, or vice versa. Changing the cornea's exposure from the first concentration to the second concentration changes the rate of cross-linking in the corneal tissue as desired. If the information from step 240 indicates that the first amount of $O_2$ is too low, step 250 provides a second amount of $O_2$ that is greater than the first amount of $O_2$. On the other hand, if the information from step 240 indicates that the first amount of $O_2$ is too high, step 250 provides a second amount of $O_2$ that is greater than the first amount of $O_2$. It may be necessary to remove the first amount of $O_2$, e.g., from the enclosure 510, before providing the second amount of $O_2$ in step 250.

In some cases, it may be desired to provide substantially zero $O_2$ in step 250 to minimize or reduce the amount of $O_2$ in the corneal tissue during irradiation in step 260. Accordingly, step 250 may introduce a non-$O_2$ element or substance above the corneal surface. For example, nitrogen gas ($N_2$) may replace the $O_2$ supplied by the devices 500 and 510 shown in FIGS. 11A and 11B.

Although the embodiments described above may employ Riboflavin as a cross-linking agent, it is understood that other substances may be employed as a cross-linking agent. The photoactivating light 332' may include, for example, UV light or green light.

Aspects of the cross-linking treatments described herein may be applied in combination with any eye therapy that may require additional stabilization of the corneal tissue. In some embodiments, cross-linking treatments are combined with astigmatic keratotomy eye surgery (AK). AK is a surgical procedure for correcting astigmatism, where incisions are made in the steepest part of the abnormally shaped cornea to relax the cornea into a rounded shape. AK is often employed in combination with cataract surgery. The resulting shape change from AK can be stabilized with cross-linking treatment. Similarly, cross-linking treatments may be combined with radial keratotomy (RK), which is a surgical procedure for correcting myopia, where radial incisions are made to the cornea to make corrective shape changes. In addition to stabilizing the corrective shape changes, the effect of applying the cross-linking agent may also allow smaller incisions to be used during AK or RK.

Aspects of the present disclosure relate to monitoring and optimizing the parameters of applying the cross-linking agent to the eye and of activating the cross-linking agent. A large variety of factors affect the rate of the cross-linking reaction and the amount of biomechanical stiffness achieved due to cross-linking. These factors include Riboflavin concentration, conditions on the cornea, temperature, presence of oxidizing agents, the type of illumination applied to activate the Riboflavin, the irradiance, the dose, the on/off duty cycle of the applied illumination, as well as other factors. A number of these factors are interrelated, in other words, changing one factor may have an unexpected effect on another factor.

Aspects of the present disclosure relate to determining the effect of each of these parameters on the rate and the amount of cross-linking, as well as the interrelations of these parameters among each to optimize the conditions to achieve the desired amount, rate, and location of corneal stiffening. Aspects of the present disclosure relate to monitoring the corneal response to a change in one or a plurality of parameters and adjusting the one or the plurality of parameters based on the received feedback.

Although the embodiments described above may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be "substantially" stepwise where there may be more gradual transitions between on/off values. In addition, it is understood that irradiance does not have to decrease down to a value of zero during the off cycle, and may be above zero during the off cycle. Effects of the present disclosure may be achieved by applying light to the cornea according to a curve varying irradiance between two or more values.

While the present disclosure has been described in connection with a number of exemplary embodiments, and implementations, the present disclosure is not so limited, but rather covers various modifications, and equivalent arrangements. In addition, although aspects of the present invention may be described in separate embodiments, it is contemplated that the features from more than one embodiment described herein may be combined into a single embodiment.

What is claimed is:

1. A system for dynamically controlling an amount of cross-linking in a cornea, comprising:
   a light source configured to activate cross-linking activity in a selected region of a cornea treated with a cross-linking agent, the light source being configured to deliver pulsed light illumination according to parameters including at least one of a frequency, an irradiance, a dose, or an on/off duty cycle; and
   a controller coupled to the light source and configured to determine, based on a proposed set of the parameters for the light source, a calculated amount of cross-linking activity generated by reactions not involving singlet molecular oxygen and to adjust one or more of the parameters for the light source according at least to the calculated amount of cross-linking activity, in order to generate a desired amount of cross-linking activity in the selected region of the cornea,
   wherein the controller is configured to cause the light source to apply the pulsed light illumination to the selected region of the cornea according at least to the one or more adjusted parameters.

2. The system of claim 1, further comprising a delivery device configured to provide a concentration of oxygen to a surface of the cornea.

3. The system of claim 2, wherein the delivery device is configured to first provide a first gas mixture that determines a first O₂ content in the cornea and secondly provide a second gas mixture that determines a second O₂ content in the cornea, the first gas mixture and the second gas mixture providing different amounts of O₂, the delivery device providing dynamic control of cross-linking in the cornea.

4. The system of claim 2, wherein the delivery device is configured to adjust an amount of oxygen delivered to the surface of the cornea according to the calculated amount of cross-linking activity generated by reactions not involving singlet molecular oxygen.

5. The system of claim 4, wherein the delivery device is configured to reduce the amount of oxygen delivered to the surface of the cornea.

6. The system of claim 2, wherein the delivery device is configured to provide a plurality of different, non-zero concentrations of oxygen to the surface of the eye, and the controller is configured to determine one of the plurality of concentrations of oxygen and cause the delivery device to provide the determined one of the plurality of concentrations of oxygen to the surface of the eye.

7. The system of claim 1, wherein the irradiance is between approximately 1 mW/cm² to approximately 500 mW/cm² and the on/off duty cycle is between approximately 100/1 to approximately 1/100.

8. The system of claim 1, wherein the pulsed light illumination has a pulse rate between approximately 0.1 Hz to approximately 1000 Hz.

9. The system of claim 1, wherein the irradiance is between approximately 1 mW/cm² to approximately 1000 mW/cm² and the on/off duty cycle is between approximately 1000/1 to approximately 1/1000.

10. The system of claim 1, wherein the pulsed light illumination has a pulse rate between approximately 1000 Hz to approximately 100,000 Hz.

11. The system of claim 1, wherein the light source is further configured to apply the pulsed light illumination to different regions of the cornea according to different respective on/off duty cycles in response to the controller.

12. The system of claim 1, wherein the light source is further configured to apply the pulsed light illumination and continuous wave illumination to different regions of the cornea according to different respective on/off duty cycles in response to the controller.

13. The system of claim 1, wherein the pulsed light illumination corresponds to absorption peaks of the cross-linking agent.

14. The system of claim 1, wherein the cross-linking agent includes Riboflavin with a concentration of Riboflavin between about 0.001% to about 1%.

15. The system of claim 14, wherein the controller determines the calculated amount of cross-linking activity from reactions not involving singlet molecular oxygen by determining a reaction between triple excited Riboflavin and a corneal substrate.

16. The system of claim 15 wherein, the controller adjusts one or more of the parameters for the light source to control a rate of return of the reduced form of Riboflavin to the ground state.

17. The system of claim 14, wherein the controller determines the calculated amount of cross-linking activity according at least to the following reactions:

$$Rf_3^* + SH \rightarrow RfH\cdot + S\cdot, \text{ and}$$

$$2RfH\cdot \rightarrow Rf + RfH_2,$$

where Rf represents Riboflavin in a ground state, Rf represents Riboflavin in a triplet excited state, RfH. represents a radical form of Riboflavin, RfH₂ represents a reduced form of Riboflavin, SH represents a corneal substrate, and S. represent a corneal substrate radical.

18. The system of claim 1, wherein the light source applies the pulsed light illumination according to a selected pattern corresponding to the selected region of the cornea.

19. The system of claim 1, wherein the controller further determines the calculated amount of cross-linking activity based at least on one of a proposed concentration of the cross-linking agent or a proposed soak time for the treatment of the cross-linking agent.

20. The system of claim 1, wherein the controller adjusts one or more of the parameters for the light source to increase an actual amount of cross-linking activity generated by reactions not involving singlet molecular oxygen.

21. The system of claim 1, wherein the light source includes a digital micro-mirror device (DMD) including a plurality of mirrors, each mirror representing one or more pixels for the pulsed light illumination.

* * * * *